US007745185B1

(12) United States Patent
Thomae et al.

(10) Patent No.: US 7,745,185 B1
(45) Date of Patent: Jun. 29, 2010

(54) SULFOTRANSFERASE 1A3 SEQUENCE VARIANTS

(75) Inventors: Bianca A. Thomae, Chicago, IL (US); Eric D. Wieben, Rochester, MN (US); Richard M. Weinshilboum, Rochester, MN (US)

(73) Assignee: Mayo Foundation for Medical Education and Research, Rochester, NM (US)

( * ) Notice: Subject to any disclaimer, the term of this patent is extended or adjusted under 35 U.S.C. 154(b) by 207 days.

(21) Appl. No.: 12/127,110

(22) Filed: May 27, 2008

Related U.S. Application Data

(63) Continuation of application No. 10/348,546, filed on Jan. 21, 2003, now Pat. No. 7,425,624.

(51) Int. Cl.
   C12N 9/00     (2006.01)
   C12N 9/10     (2006.01)
   C07K 14/00    (2006.01)
   C07K 17/00    (2006.01)

(52) U.S. Cl. .................. 435/183; 435/193; 530/350

(58) Field of Classification Search .................. None
   See application file for complete search history.

(56) References Cited

U.S. PATENT DOCUMENTS

| 5,451,683 A | 9/1995 | Barrett et al. |
| 5,733,729 A | 3/1998 | Lipshutz et al. |
| 5,770,722 A | 6/1998 | Lockhart et al. |
| 6,448,003 B1 | 9/2002 | Guida et al. |
| 6,812,339 B1 | 11/2004 | Venter et al. |
| 2001/0053519 A1 | 12/2001 | Fodor et al. |

FOREIGN PATENT DOCUMENTS

| WO | WO 98/20019 | 5/1998 |
| WO | WO 99/57318 | 11/1999 |
| WO | WO 99/64630 | 12/1999 |
| WO | WO 00/20605 | 4/2000 |
| WO | WO 01/94629 | 12/2001 |

OTHER PUBLICATIONS

GenBank Accession No. L19956, dated Oct. 14, 1993, 2 pages.
GenBank Accession No. U20499, dated Mar. 29, 1995, 4 pages.
Chin, "On the preparation and utilization of isolated and purified oligonucleotides," University of North Carolina, Mar. 9, 2002 (on CD due to large volume of pages).
Cibelli et al., "Cloned Transgenic Calves Produced from Nonquiescent Fetal Fibroblasts," *Science*, 1998, 280:1256-1258.
Cleland, "Computer Programmes for Processing Enzyme Kinetic Data," *Nature*, 1963, 198(4879):463-465.
Cole et al., "The EBV-Hybridoma Technique and Its Application to Human Lung Cancer," *Monoclonal Antibodies and Cancer Therapy*, 1985, pp. 77-96.
Cote et al., "Generation of human monoclonal antibodies reactive with cellular antigens," *Proc. Natl. Acad. Sci. USA*, 1983, 80:2026-2030.
Dajani et al., "X-ray Crystal Structure of Human Dopamine Sulfotransferase, SULT1A3," *J. Biol. Chem.*, 1999, 274(53):37862-37868.
Dajani et al., "Kinetic Properties of Human Dopamine Sulfotransferase (SULT1A3) Expressed in Prokaryotic and Eukaryotic Systems: Comparison with the Recombinant Enzyme Purified from *Escherichia coli*," *Protein Expressions and Purifications*, 1999, 16:11-18.
Dubin et al., "Thermostable (SULT1A1) and Thermolabile (SULT1A3) Phenol Sulfotransferases in Human Osteosarcoma and Osteoblast Cells," *Bone*, 2001, 28(6):617-624.
Excoffier and Slatkin, "Maximum-Likelihood Estimation of Molecular Haplotype Frequencies in a Diploid Population," *Mol. Biol. Evol.*, 1995, 12(5):921-927.
Glatt et al., "Human cytosolic sulphotransferases: genetics, characteristics, toxicological aspects," *Mutation Research*, 2001, 482:27-40.
Guatelli et al., "Isothermal, in vitro amplication of nucleic acids by a nultienzyme reaction modeled after retroviral replication," *Proc. Natl. Acad. Sci. USA*, 1990, 87:1874-1878.
Hacia et al., "Detection of heterozygous mutations in *BRCA1* using high density oligonucleotide arrays and two-colour fluorescence analysis," *Nature Genetics*, 1996, 14:441-447.
Halushka et al., "Patterns of single-nucleotide polymorphisms in candidate genes for blood-pressure homeostasis," *Nature Genetics*, 1999, 22:239-247.
Hartl and Clark, *Principles of Population Genetics*, 3rd Edition, 1997, Sinauer Associates, Sunderland, MA, pp. 96-106.
Hedrick, *Genetics of Populations*, 2000, Jones and Bartlett Publishers, Sudbury, MA, pp. 396-405.
Hildebrandt et al., "Human SULT1A3 pharmacogenetics: gene duplication and functional genomic studies," *Biochem. Biophys. Res. Comm.*, 2004, 321:870-878.
Ho et al., "Site-directed mutagenesis by overlap extension using the polymerase chain reaction," *Gene*, 1989, 77:51-59.
Honma et al., "Phenol Sulfotransferase, ST1A3, as the Main Enzyme Catalyzing Sulfation of Troglitazone in Human Liver," *Drug Metabolism and Disposition*, 2002, 30:944-949.
Huse et al., "Generation of a Large Combinatorial Library of the Immunoglobulin Repertoire in Phage Lambda," *Science*, 1989, 246:1275-1281.
Hyrup and Nielsen, "Peptide Nucleic Acids (PNA): Synthesis, Properties and Potential Applications," *Bioorganic & Medicinal Chemistry*, 1996, 4(1):5-23.

(Continued)

*Primary Examiner*—Suzanne M. Noakes
*Assistant Examiner*—Jae W Lee
(74) *Attorney, Agent, or Firm*—Fish & Richardson P.C.

(57) ABSTRACT

Isolated sulfotransferase 1A3 nucleic acid molecules and polypeptides that include nucleotide sequence variants and amino acid sequence variants are described. Methods for determining predisposition to particular clinical conditions and methods for determining sulfonator status also are described.

2 Claims, 16 Drawing Sheets

OTHER PUBLICATIONS

Iida et al., "Catalog of 320 single nucleotide polymorphisms (SNPs) in 20 quinone oxidoreductase and sulfotransferase genes," *J. Hum. Genet.*, 2001, 46:225-240.

Köhler and Milstein, "Continuous cultures of fused cells secreting antibody of predefined specificity," *Nature*, 1975, 256:495-497.

Kozbor and Roder, "The production of monoclonal antibodies from human lymphocytes," *Immunology Today*, 1983, 4(3):72-79.

Kreis et al., "Human phenol sulfotransferases hP-PST and hM-PST activate propane 2-nitronate to a genotoxicant," *Carcinogenesis*, 2000, 21(2):295-299.

Long et al., "An E-M Algorithm and Testing Strategy for Multiple-Locus Haplotypes," *Am. J. Hum. Genet.*, 1995, 56:799-810.

Myakishev et al., "High-Throughput SNP Genotyping by Allele-Specific PCR with Universal Energy-Transfer-Labeled Primers," *Genome Research*, 2001, 11:163-169.

Pai et al., "Sulfation of Flavonoids and Other Phenolic Dietary Compounds by the Human Cytosolic Sulfotransferases," *Biochem. Biophys. Res. Commun.*, 2001, 285:1175-1179.

Prince et al., "Robust and Accurate Single Nucleotide Polymorphism Genotyping by Dynamic Allele-Specific Hybridization (DASH): Design Criteria and Assay Validation," *Genome Research*, 2001, 11:152-162.

Raftogianis et al., "Phenol Sulfotransferase Pharmacogenetics in Humans: Association of Common *SULT1A1* Alleles with TS PST Phenotype," *Biochem. Biophys. Res. Commun.*, 1997, 239:298-304.

Richard et al., "Sulfation of Thyroid Hormone and Dopamine during Human Development: Ontogeny of Phenol Sulfotransferases and Arylsulfatase in Liver, Lung, and Brain," *J. Clin. Endocrinol. Metab.*, 2001, 86(6):2734-2742.

Rubin et al., "Regulation of sulphotransferase expression in the endometrium during the menstrual cycle, by oral contraceptives and during early pregnancy," *Mol. Hum. Reprod.*, 1999, 5:995-1002.

Schafer and Hawkins, "DNA variation and the future of human genetics," *Nature Biotech.*, 1998, 16:33-39.

Shastry, "Gene disruption in mice: Models of development and diseasse," *Mol. Cell. Biochem.*, 1998, 181:163-179.

Stoneking et al., "Population Variation of Human mtDNA Control Region Sequences Detected by Enzymatic Amplification and Sequence-specific Oligonucleotide Probes," *Am. J. Hum. Genet.*, 1991, 48:370-382.

Summerton and Weller, "Morpholino Antisense Oligomers: Design, Preparation, and Properties," *Antisense & Nucleic Acid Drug Development*, 1997, 7:187-195.

Terwilliger and Ott, *Handbook of Human Genetic Linkage*, 1994, The Johns Hopkins University Press, Baltimore and London, pp. 188-193.

Thomae et al., "Human catecholamin sulfotransferase (SULT1A3) pharmacogenetics: functional genetic polymorphism," *J. Neurochemistry*, 2003, 87:809-819.

Underhill et al., "Detection of Numerous Y Chromasome Biallelic Polymorphisms by Denaturing High-Performance Liquid Chromatography," *Genome Res.*, 1997, 7:996-1005.

Van Loon et al., "Thiopurine Methyltransferase Isozymes in Human Renal Tissue," *Drug Metabolism and Disposition*, 1990, 18(5):632-638.

Van Loon et al., "Human Kidney Thiopurine Methyltransferase," *Biochem. Pharmacol.*, 1992, 44(4):775-785.

Wakayama et al., "Full-term development of mice from enucleated oocytes injected with cumulus cell nuclei," *Nature*, 1998, 394:369-374.

Weiss, "Hot Prospect for New Gene Amplifier," *Science*, 1991, 254:1292-1293.

Wilkinson, "Statistical Estimations in Enzyme Kinetics," *Biochem. J.*, 1961, 80:324-332.

Williams et al., "*N*-Acetyltransferases, sulfotransferases and heterocyclic amine activation in the breast," *Pharmacogenetics*, 2001, 11:373-388.

Wilmut et al., "Viable offspring derived from fetal and adult mammalian cells," *Nature*, 1997, 385:810-813.

Wong et al., "Human GM-CSF: Molecular Cloning of the Complementary DNA and Purification of the Natural and Recombinant Proteins," *Science*, 1985, 228:810-815.

Wood et al., "Human Liver Thermolabile Phenol Sulfotransferase: cDNA Cloning, Expression and Characterization," *Biochem. Biophys. Res. Commun.*, 1994, 198:1119-1127.

Figure 1 – page 1

```
       ACCTCTGCCTCCTGGTTCCAAGCAATCCTCCTTCCTCACCCTCCAGAGTAGCTGGGATTA
  1    ---------+---------+---------+---------+---------+---------+   60
       TGGAGACGGAGGACCAAGGTTCGTTAGGAGGAAGGAGTGGGAGGTCTCATCGACCCTAAT

CACGCGCCTGCCACCGCGCCTGGCCTAATTTTTGTATTTTTAGTAGAGATGGGGGTTTCC
 61    ---------+---------+---------+---------+---------+---------+  120
       GTGCGCGGACGGTGGCGCGGACCGGATTAAAAACATAAAAATCATCTCTACCCCCAAAGG

AACCATGTTGGCCAGGCTGGTCTCCAAACTCCTGACCTCAGGTGATCCTGCCCACCTAAG
121    ---------+---------+---------+---------+---------+---------+  180
       TTGGTACAACCGGTCCGACCAGAGGTTTGAGGACTGGAGTCCACTAGGACGGGTGGATTC

CCTCCCAAAATGCTGGTATTACAGGCATGAGCCACCGTGCCCGGCCTAAATAATTAATAA
181    ---------+---------+---------+---------+---------+---------+  240
       GGAGGGTTTTACGACCATAATGTCCGTACTCGGTGGCACGGGCCGGATTTATTAATTATT

AATAATGGACGATGGGTGCCTTCTACTGAGCTCCCGGTAATTGTGAGTGAGTAGAGGACT
241    ---------+---------+---------+---------+---------+---------+  300
       TTATTACCTGCTACCCACGGAAGATGACTCGAGGGCCATTAACACTCACTCATCTCCTGA

TGCCCTGGGGACATTCAGTGACCTGCTGGGTGTTGCTGAGCTGTGAGGAAGTTCAGGTCT
301    ---------+---------+---------+---------+---------+---------+  360
       ACGGGACCCCTGTAAGTCACTGGACGACCCACAACGACTCGACACTCCTTCAAGTCCAGA

GGCTGCAGTGGTGAGGCTGTGACTCAATCAATCACTGCTGATGCTCCCAGGACCTGCACC
361    ---------+---------+---------+---------+---------+---------+  420
       CCGACGTCACCACTCCGACACTGAGTTAGTTAGTGACGACTACGAGGGTCCTGGACGTGG

AGCTTAGTCCTAGGGGCAAGGATTTTAACTGTCCACCTCAGTTTCTTCATTTGTAAGATG
421    ---------+---------+---------+---------+---------+---------+  480
       TCGAATCAGGATCCCCGTTCCTAAAATTGACAGGTGGAGTCAAAGAAGTAAACATTCTAC

CAAATAACAGTCACCCCTGCCTCATGGGATGGAGCTGTGTAATGCCCGCAACAGTGCCTG
481    ---------+---------+---------+---------+---------+---------+  540
       GTTTATTGTCAGTGGGGACGGAGTACCCTACCTCGACACATTACGGGCGTTGTCACGGAC

CTGCATAGAGGGGTTGCTGCCAGCTGCCTCTCCCTCCTTGTCTCTTACCTGCCTGCTGCC
541    ---------+---------+---------+---------+---------+---------+  600
       GACGTATCTCCCCAACGACGGTCGACGGAGAGGGAGGAACAGAGAATGGACGGACGACGG

EXON 1C
       TGGGTCAGGATGAAGAGGGGCCCTTGTGTTGCCCCCACCCTGGCTGCCTGCTAAGGGCCC
601    ---------+---------+---------+---------+---------+---------+  660
       ACCCAGTCCTACTTCTCCCCGGGAACACAACGGGGGTGGGACCGACGGACGATTCCCGGG

ATGTGATCTGCCTGGCAGAGGAGTTTCTTCAGGAAGAACCAGGGCAGCTTCTGCCCCTAG
661    ---------+---------+---------+---------+---------+---------+  720
       TACACTAGACGGACCGTCTCCTCAAAGAAGTCCTTCTTGGTCCCGTCGAAGACGGGGATC

AGGGCCAATGCCCTTGGTGAGTGCAGTCCCCTGGCCCCAGCCTGGTCCACCTCTGGGAAG
721    ---------+---------+---------+---------+---------+---------+  780
       TCCCGGTTACGGGAACCACTCACGTCAGGGGACCGGGGTCGGACCAGGTGGAGACCCTTC
```

Figure 1 – page 2

```
                                                      C(I1C96)T  G(I1C99)C
       AGGGTGCCCAGTTGTGCAATCCAGGCCCAGGCAGCTGAGCCCTCATCTCAGCATGCAGGG
  781  ---------+---------+---------+---------+---------+---------+  840
       TCCCACGGGTCAACACGTTAGGTCCGGGTCCGTCGACTCGGGAGTAGAGTCGTACGTCCC

C(I1C105)T
       CGGATACTGGAGGGGGCTTGTGGCATCTGACTCTGTATCTCCTACCTGCCCCTCTCCTTG
  841  ---------+---------+---------+---------+---------+---------+  900
       GCCTATGACCTCCCCCGAACACCGTAGACTGAGACATAGAGGATGGACGGGGAGAGGAAC

EXON 1B
       GTAGCTGTGAGAAGTCACTGCTTTGGGGAGACCTGATCTGGCTGTGCCAGATGGACACTG
  901  ---------+---------+---------+---------+---------+---------+  960
       CATCGACACTCTTCAGTGACGAAACCCCTCTGGACTAGACCGACACGGTCTACCTGTGAC

AGAAAGAAGTAGAAGACTCAGAATTAGAAGAGGTGAGTGGGCTTTGGTGGCGGGCTCCCT
  961  ---------+---------+---------+---------+---------+---------+ 1020
       TCTTTCTTCATCTTCTGAGTCTTAATCTTCTCCACTCACCCGAAACCACCGCCCGAGGGA

ACCCCACTCCCTGCCCTGGGCTGCCTGTGACCACACTGCTTGCCTCTGCAGGCACACTGG
 1021  ---------+---------+---------+---------+---------+---------+ 1080
       TGGGGTGAGGGACGGGACCCGACGGACACTGGTGTGACGAACGGAGACGTCCGTGTGACC

ACAGACCTGCTGGAGACCTGATCCTCAGTGTCCTTACCCCCTCCTACCTCTTTTCTGTGC
 1081  ---------+---------+---------+---------+---------+---------+ 1140
       TGTCTGGACGACCTCTGGACTAGGAGTCACAGGAATGGGGGAGGATGGAGAAAAGACACG

CACCTGCTGTGGGTCCAGCAGGTTTTTACTTGAGTACAATAAAAAGTCTGAGTCAAGGGT
 1141  ---------+---------+---------+---------+---------+---------+ 1200
       GTGGACGACACCCAGGTCGTCCAAAAATGAACTCATGTTATTTTTCAGACTCAGTTCCCA

GCCTTATGGTGGATGCTGAGGGGAGGGGCGGAGCTAGTAGCCCAAGGTCCTGCCAGTCAC
 1201  ---------+---------+---------+---------+---------+---------+ 1260
       CGGAATACCACCTACGACTCCCCTCCCCGCCTCGATCATCGGGTTCCAGGACGGTCAGTG

GGGGCTTCCTCAGGGGCACAGAGGAGGCAGGAGGGGCCCCTGGCCCTAGCACGTGAACAG
 1261  ---------+---------+---------+---------+---------+---------+ 1320
       CCCCGAAGGAGTCCCCGTGTCTCCTCCGTCCTCCCCGGGGACCGGGATCGTGCACTTGTC

CTTCTACTCTGCCTGGAAACCCCATGCCTCAGCTTTCCCCTACTTGCCTCTGAGCTCATG
 1321  ---------+---------+---------+---------+---------+---------+ 1380
       GAAGATGAGACGGACCTTTGGGGTACGGAGTCGAAAGGGGATGAACGGAGACTCGAGTAC

CAATTCTTGGAAGCCTGGGAGACTTACCTTGAAATTGAATGCAAATAGGACAAAGACCAA
 1381  ---------+---------+---------+---------+---------+---------+ 1440
       GTTAAGAACCTTCGGACCCTCTGAATGGAACTTTAACTTACGTTTATCCTGTTTCTGGTT

GGAGGATGGGGGGATGCCCTCCTTCCACGGGCCCTGTGGCTTCCAAGTCTTAATCTCCT
 1441  ---------+---------+---------+---------+---------+---------+ 1500
       CCTCCTACCCCCCTACGGGAGGAAGGTGCCCCGGGACACCGAAGGTTCAGAATTAGAGGA
```

Figure 1 – page 3

```
     CTAGTCTCTTGTCTACGGAGCCTCCTTCAAACCCAGGGAAAGAAAAGCACCTGCCAGGGT
1501 ---------+---------+---------+---------+---------+---------+ 1560
     GATCAGAGAACAGATGCCTCGGAGGAAGTTTGGGTCCCTTTCTTTTCGTGGACGGTCCCA

TGTTTTTCTTCTAGGATCTTCTATTGATGCTCTGTGAGGTCCCCCAGGAGCCATGAAGCT
1561 ---------+---------+---------+---------+---------+---------+ 1620
     ACAAAAAGAAGATCCTAGAAGATAACTACGAGACACTCCAGGGGGTCCTCGGTACTTCGA

AGGGCTGGCTCCTAGGGCAATGGGACTACAGTGTCCTTGTCCTTTCTTATTCTTTCTGTT
1621 ---------+---------+---------+---------+---------+---------+ 1680
     TCCCGACCGAGGATCCCGTTACCCTGATGTCACAGGAACAGGAAAGAATAAGAAAGACAA

CTTTCTTTCTTTCTTTTTTTTTTTTTTTTTTTTTTTGAGACAGAGTCTCACTCTGTTGC
1681 ---------+---------+---------+---------+---------+---------+ 1740
     GAAAGAAAGAAAGAAAAAAAAAAAAAAAAAAAAAAAACTCTGTCTCAGAGTGAGACAACG

CCAGGCTGGAGTGCAGTGGTGTGATCTTGGCTCACTGAAACCTCCGCCTCCTGGGTTCAA
1741 ---------+---------+---------+---------+---------+---------+ 1800
     GGTCCGACCTCACGTCACCACACTAGAACCGAGTGACTTTGGAGGCGGAGGACCCAAGTT

GTGATTCTCTTGCCTCAGCCTCCTGAGTAGCTAGGATTACAGGTGCCCGCCATCATGCCC
1801 ---------+---------+---------+---------+---------+---------+ 1860
     CACTAAGAGAACGGAGTCGGAGGACTCATCGATCCTAATGTCCACGGGCGGTAGTACGGG

AGCTAATTTTTGTATTTTTAGTAGAGACAGGGTTTCACCATGTTGGCCAGCTTGGTCTCG
1861 ---------+---------+---------+---------+---------+---------+ 1920
     TCGATTAAAAACATAAAAATCATCTCTGTCCCAAAGTGGTACAACCGGTCGAACCAGAGC

AACTCCTGACCTCAGGTGATCCTGCTGCATCGACCTCCCAAAGTACTGGGATTACAGGCG
1921 ---------+---------+---------+---------+---------+---------+ 1980
     TTGAGGACTGGAGTCCACTAGGACGACGTAGCTGGAGGGTTTCATGACCCTAATGTCCGC

TGAGCCACCACGCTCAGCCTCTTTCTTGTTCTATATGTCCATGCTCTGCTCCACTTCTGC
1981 ---------+---------+---------+---------+---------+---------+ 2040
     ACTCGGTGGTGCGAGTCGGAGAAAGAACAAGATATACAGGTACGAGACGAGGTGAAGACG

CCCTTCACTCTGCCCCACACATCACTCCAGACTGGCCTTGTGGTCAGAGCCTGGAATGCC
2041 ---------+---------+---------+---------+---------+---------+ 2100
     GGGAAGTGAGACGGGGTGTGTAGTGAGGTCTGACCGGAACACCAGTCTCGGACCTTACGG

TGGGCTGCTGGGGGCCTGTGGACTGCACTGGGCCAGAACCCCTGCCGCCTTCAAGACTGG
2101 ---------+---------+---------+---------+---------+---------+ 2160
     ACCCGACGACCCCCGGACACCTGACGTGACCCGGTCTTGGGGACGGCGGAAGTTCTGACC

CCTGTAGCCAGCAGGTAGGTGACTTTTCCCAGGCCGGCCTATCCCACCTTTCCCCTCCAC
2161 ---------+---------+---------+---------+---------+---------+ 2220
     GGACATCGGTCGTCCATCCACTGAAAAGGGTCCGGCCGGATAGGGTGGAAAGGGGAGGTG

TCACTCACCTCCCTTGCCTGGGTCAATTAGAGAAAGCTTGTCGGCCAGGCATGGTGGCTC
2221 ---------+---------+---------+---------+---------+---------+ 2280
     AGTGAGTGGAGGGAACGGACCCAGTTAATCTCTTTCGAACAGCCGGTCCGTACCACCGAG
```

Figure 1 – page 4

```
        ATGCCTGTAATCTCAGCACTTTGGGAGGCCGAGGCGGGCGGATCATCTGAGCTCAGGAGT
2281    ---------+---------+---------+---------+---------+---------+ 2340
        TACGGACATTAGAGTCGTGAAACCCTCCGGCTCCGCCCGCCTAGTAGACTCGAGTCCTCA

TTGAGACCAGCCTGGCCAACATGGCAAAACCCCGTCTCTACTAAAAATACAAAAATTAAC
2341    ---------+---------+---------+---------+---------+---------+ 2400
        AACTCTGGTCGGACCGGTTGTACCGTTTTGGGGCAGAGATGATTTTTATGTTTTTAATTG

CGGATGTGGTGGTGTGCACCTGTAATCCCAGCTACTCGGGAGGCTGAGGCAGAAGAATCG
2401    ---------+---------+---------+---------+---------+---------+ 2460
        GCCTACACCACCACACGTGGACATTAGGGTCGATGAGCCCTCCGACTCCGTCTTCTTAGC

CTTGAACCCAGGAGGGGGAGGTTACAGTGAGCGGAGATCGTGCTACTGCATTGCAGCCTG
2461    ---------+---------+---------+---------+---------+---------+ 2520
        GAACTTGGGTCCTCCCCCTCCAATGTCACTCGCCTCTAGCACGATGACGTAACGTCGGAC

GGCGAGAGAGCGAGTCTCCATCTCACATAAAAAAAAGAAAAAGAAAGAAAGCAAGCTTGT
2521    ---------+---------+---------+---------+---------+---------+ 2580
        CCGCTCTCTCGCTCAGAGGTAGAGTGTATTTTTTTCTTTTTCTTTCTTTCGTTCGAACA

CTGTTGGCCTGCCCTGCAGGGTGGAGTTCAGAGGGAAGGTCAGGAGCCTAGTGACAGCTC
2581    ---------+---------+---------+---------+---------+---------+ 2640
        GACAACCGGACGGGACGTCCCACCTCAAGTCTCCCTTCCAGTCCTCGGATCACTGTCGAG

AAAAAAAAAAAAACCCAAATACCAATGTTGGCCCCTTTTGCCTTTCATTCATGTGTTTTC
2641    ---------+---------+---------+---------+---------+---------+ 2700
        TTTTTTTTTTTTTGGGTTTATGGTTACAACCGGGGAAAACGGAAAGTAAGTACACAAAAG

TATACACTAAACTCACATATTGGGTTTGCAGATCACTCCAAGCTTGGCTGGAGCTGTGGT
2701    ---------+---------+---------+---------+---------+---------+ 2760
        ATATGTGATTTGAGTGTATAACCCAAACGTCTAGTGAGGTTCGAACCGACCTCGACACCA

GGTAAGGAGGGTAATAGAGAAGCTTCCCCACCCTCAACCCCACCCCTTCCTTCCTGGAGT
2761    ---------+---------+---------+---------+---------+---------+ 2820
        CCATTCCTCCCATTATCTCTTCGAAGGGGTGGGAGTTGGGGTGGGGAAGGAAGGACCTCA

EXON 1A
        TCCCAGCCCTGACTTTAGATCCCTCCCACACTGGACCTTCAAAACCCTCAGGGCAGAGAG
2821    ---------+---------+---------+---------+---------+---------+ 2880
        AGGGTCGGGACTGAAATCTAGGGAGGGTGTGACCTGGAAGTTTTGGGAGTCCCGTCTCTC

CAGCCCTACACTCCCTACACCACACCCATACTCAGCCCCTGCAGGCAAGGAGAGAACAGG
2881    ---------+---------+---------+---------+---------+---------+ 2940
        GTCGGGATGTGAGGGATGTGGTGTGGGTATGAGTCGGGGACGTCCGTTCCTCTCTTGTCC

TCAGGTTCCCGAGAGCTCAGGTGAGTGACACGTTGGAATGGCCCAGGGCACCTTCACCCT
2941    ---------+---------+---------+---------+---------+---------+ 3000
        AGTCCAAGGGCTCTCGAGTCCACTCACTGTGCAACCTTACCGGGTCCCGTGGAAGTGGGA

GCTCAGCTTGTGGCTCCAACATTCTAGAAGCCGAGGCCTCTGCCATCCCTGCCCTTTCCC
3001    ---------+---------+---------+---------+---------+---------+ 3060
        CGAGTCGAACACCGAGGTTGTAAGATCTTCGGCTCCGGAGACGGTAGGGACGGGAAAGGG
```

Figure 1 – page 5

```
      ATGGATATTCCATTTCAATTAGACAACCCAGCCTGGCCGGAATCCCCCTGCGTTCCTTCT
3061  ---------+---------+---------+---------+---------+---------+ 3120
      TACCTATAAGGTAAAGTTAATCTGTTGGGTCGGACCGGCCTTAGGGGGACGCAAGGAAGA

TTTCCTTTGTGTATTTTTGAGACAGGGTGTTGCTCCGTCACCCAGGCTGGAGTGTAGTGG
3121  ---------+---------+---------+---------+---------+---------+ 3180
      AAAGGAAACACATAAAAACTCTGTCCCACAACGAGGCAGTGGGTCCGACCTCACATCACC

GATCCTGGCCCACTGCAGCCTCAAATTCCTAGGCTGAGGCAATCCTGCCGCCTCAGCCTC
3181  ---------+---------+---------+---------+---------+---------+ 3240
      CTAGGACCGGGTGACGTCGGAGTTTAAGGATCCGACTCCGTTAGGACGGCGGAGTCGGAG

CTGAGTAGCTGGGGTTACAAGAGCAAGCCACCACACCCAGCTAATTTTGAAAAATATTTT
3241  ---------+---------+---------+---------+---------+---------+ 3300
      GACTCATCGACCCCAATGTTCTCGTTCGGTGGTGTGGGTCGATTAAAACTTTTTATAAAA

TTGTAGAGGAGAGGTCTTGCTTTGTTGTCCAGGTTGGTCTCAAACTCCAGGGCTCAAGGG
3301  ---------+---------+---------+---------+---------+---------+ 3360
      AACATCTCCTCTCCAGAACGAAACAACAGGTCCAACCAGAGTTTGAGGTCCCGAGTTCCC

ATCCTTTCCCGTTGGCCTCCCAAGGCTCTGGGATTACAGGCGGGAGTCACCCTGCCTGGG
3361  ---------+---------+---------+---------+---------+---------+ 3420
      TAGGAAAGGGCAACCGGAGGGTTCCGAGACCCTAATGTCCGCCCTCAGTGGGACGGACCC

CCCCTCCTTTTGATGAGTCATCAGTTTTCATTCCCGCACGAGGCTCTAGCCCCTGGTACC
3421  ---------+---------+---------+---------+---------+---------+ 3480
      GGGGAGGAAAACTACTCAGTAGTCAAAAGTAAGGGCGTGCTCCGAGATCGGGGACCATGG

AGCTTAGTTGCTCAATGGGCTGTGTTTGTTCTGGAGCCCAGATGGACTGTGGCCAGGCAA
3481  ---------+---------+---------+---------+---------+---------+ 3540
      TCGAATCAACGAGTTACCCGACACAAACAAGACCTCGGGTCTACCTGACACCGGTCCGTT

GTGGATCACAGACCTGGCCGGCCTGGGAGGTTTCCACATGTGAGGGGCATGAGGGGGGCT
3541  ---------+---------+---------+---------+---------+---------+ 3600
      CACCTAGTGTCTGGACCGGCCGGACCCTCCAAAGGTGTACACTCCCCGTACTCCCCCCGA

CAAGGAGGGGAGCATCGGGGAGAGGAGCGCACTGGGTGGAGGCTGGGGGTCCCAGCAGGA
3601  ---------+---------+---------+---------+---------+---------+ 3660
      GTTCCTCCCCTCGTAGCCCCTCTCCTCGCGTGACCCACCTCCGACCCCCAGGGTCGTCCT

AATGGTGAGACAAAGGGCGCTGGCTGGCAGGGAGACAGCACAGGCAGGCCCTAGAGCTTC
3661  ---------+---------+---------+---------+---------+---------+ 3720
      TTACCACTCTGTTTCCCGCGACCGACCGTCCCTCTGTCGTGTCCGTCCGGGATCTCGAAG

CTCAGCACAGCTGGACTCTCCTGGAGACCTTCACACACCCTGATATCTGGGCCCCGCGCT
3721  ---------+---------+---------+---------+---------+---------+ 3780
      GAGTCGTGTCGACCTGAGAGGACCTCTGGAAGTGTGTGGGACTATAGACCCGGGGCGCGA

ACGAGGGTGCTTTCACTGGTCTGCACTATGCCCCAGGCCCTGGGATTTTGAACAGCTCTG
3781  ---------+---------+---------+---------+---------+---------+ 3840
      TGCTCCCACGAAAGTGACCAGACGTGATACGGGGTCCGGGACCCTAAAACTTGTCGAGAC
```

Figure 1 – page 6

```
      CAGGTGACTGAAAGGTGCGGCCAGGCTGGGGAACGACCTGGTTTCAGCCCCAGCCCCGCC
3841  ---------+---------+---------+---------+---------+---------+ 3900
      GTCCACTGACTTTCCACGCCGGTCCGACCCCTTGCTGGACCAAAGTCGGGGTCGGGGCGG

ACTGACTGACTTTGTGAGTGCGGGCAAGTCACTCAGCCTCCCTAGGCCTCAGTGACTTCC
3901  ---------+---------+---------+---------+---------+---------+ 3960
      TGACTGACTGAAACACTCACGCCCGTTCAGTGAGTCGGAGGGATCCGGAGTCACTGAAGG

CTGAAAGCAAAAACTCTGCAAAGGGGCAGCTGGGTGCTGGCTCACACCTGTAATCCCAGC
3961  ---------+---------+---------+---------+---------+---------+ 4020
      GACTTTCGTTTTTGAGACGTTTCCCCGTCGACCCACGACCGAGTGTGGACATTAGGGTCG

ACTTTGGGAGGCTGAGGTAGACAAATCACTTGAGGCCAGGAGTTCTAGACCAGCCTGGCC
4021  ---------+---------+---------+---------+---------+---------+ 4080
      TGAAACCCTCCGACTCCATCTGTTTAGTGAACTCCGGTCCTCAAGATCTGGTCGGACCGG

AACATGGTGAAACCCCATCTCTACTAAAGAAAAAAAAAAATTAGCTGAGCATGGTTGTAC
4081  ---------+---------+---------+---------+---------+---------+ 4140
      TTGTACCACTTTGGGGTAGAGATGATTTCTTTTTTTTTTAATCGACTCGTACCAACATG

ATGCTTGTAATCCCAGCTACTTGGGATGCCGAGGCGGGAGGATTGCTTGAACCCAAGAGG
4141  ---------+---------+---------+---------+---------+---------+ 4200
      TACGAACATTAGGGTCGATGAACCCTACGGCTCCGCCCTCCTAACGAACTTGGGTTCTCC

TGGAGTTTGCAGTGAGCTGAGATTGTGCCACACTGCACTCCAGCTTGGGTGAGAGTGAGA
4201  ---------+---------+---------+---------+---------+---------+ 4260
      ACCTCAAACGTCACTCGACTCTAACACGGTGTGACGTGAGGTCGAACCCACTCTCACTCT

A(I1A1325)G
      CTCCATCTCAAAAAAAAAAAAAAAAAGAGAGAATCCCACTTTCTTGCTGTTGTGATGGTG
4261  ---------+---------+---------+---------+---------+---------+ 4320
      GAGGTAGAGTTTTTTTTTTTTTTTTCTCTCTTAGGGTGAAAGAACGACAACACTACCAC

EXON 2
      GTAAGGGAACGGGCCTGGCTCTGGCCCCTGATGCAGGAACATGGAGCTGATCCAGGACAC
4321  ---------+---------+---------+---------+---------+---------+ 4380
      CATTCCCTTGCCCGGACCGAGACCGGGGACTACGTCCTTGTACCTCGACTAGGTCCTGTG

CTCCCGCCCGCCACTGGAGTACGTGAAGGGGGTCCCGCTCATCAAGTACTTTGCAGAGGC
4381  ---------+---------+---------+---------+---------+---------+ 4440
      GAGGGCGGGCGGTGACCTCATGCACTTCCCCCAGGGCGAGTAGTTCATGAAACGTCTCCG

A105G
      ACTGGGGCCCCTGCAGAGCTTCCAAGCCCGACCTGATGACCTGCTCATCAACACCTACCC
4441  ---------+---------+---------+---------+---------+---------+ 4500
      TGACCCCGGGGACGTCTCGAAGGTTCGGGCTGGACTACTGGACGAGTAGTTGTGGATGGG

CAAGTCTGGTAAGTGAGGAGGGCCACCCACCCTCTCCCAGGCGGCAGTCCCCACCTTGGT
4501  ---------+---------+---------+---------+---------+---------+ 4560
      GTTCAGACCATTCACTCCTCCCGGTGGGTGGGAGAGGGTCCGCCGTCAGGGGTGGAACCA
```

Figure 1 – page 7

EXON 3
```
        CAGCAAGGTCGTGCCCTCAGCCTGCTCACCTCCTATCTCCCTCCCTCTCCAGGCACCACC
4561    ---------+---------+---------+---------+---------+---------+ 4620
        GTCGTTCCAGCACGGGAGTCGGACGAGTGGAGGATAGAGGGAGGGAGAGGTCCGTGGTGG

TGGGTGAGCCAGATACTGGACATGATCTACCAGGGCGGCGACCTAGAGAAGTGTAACCGG
4621    ---------+---------+---------+---------+---------+---------+ 4680
        ACCCACTCGGTCTATGACCTGTACTAGATGGTCCCGCCGCTGGATCTCTTCACATTGGCC

GCTCCCATCTACGTACGGGTGCCCTTCCTTGAGGTCAATGATCCAGGGGAACCCTCAGGT
4681    ---------+---------+---------+---------+---------+---------+ 4740
        CGAGGGTAGATGCATGCCCACGGGAAGGAACTCCAGTTACTAGGTCCCCTTGGGAGTCCA

GCATGGCTGGGTCCTGGGGGTAAGGGAAGTGGAGGAAGACAGGGCTGGGGCTTCAGCTCA
4741    ---------+---------+---------+---------+---------+---------+ 4800
        CGTACCGACCCAGGACCCCCATTCCCTTCACCTCCTTCTGTCCCGACCCCGAAGTCGAGT
```

EXON 4
```
        CCAGACCTTCCCTGACCCACTACTCAGGGCTGGAGACTCTGAAAGACACACCGCCCCCAC
4801    ---------+---------+---------+---------+---------+---------+ 4860
        GGTCTGGAAGGGACTGGGTGATGAGTCCCGACCTCTGAGACTTTCTGTGTGGCGGGGGTG

GGCTCATCAAGTCACACCTGCCCCTGGCTCTGCTCCCTCAGACTCTGTTGGATCAGAAGG
4861    ---------+---------+---------+---------+---------+---------+ 4920
        CCGAGTAGTTCAGTGTGGACGGGGACCGAGACGAGGGAGTCTGAGACAACCTAGTCTTCC

TCAAGGTGAGGCCGGCCTCAATGGTTCACACCTGTCATCCCAGTTTGAGACTGAGGAGGG
4921    ---------+---------+---------+---------+---------+---------+ 4980
        AGTTCCACTCCGGCCGGAGTTACCAAGTGTGGACAGTAGGGTCAAACTCTGACTCCTCCC

AGGATCCCTTGAAGGCGAGAGATGGAGACCAGCCTGGGCAACATTGCTGTAGAGATGACA
4981    ---------+---------+---------+---------+---------+---------+ 5040
        TCCTAGGGAACTTCCGCTCTCTACCTCTGGTCGGACCCGTTGTAACGACATCTCTACTGT

TCCCATCTCTACAAAAATAAAATTAACAACCTGGTATGGTGGCATAGACTGTTCCCAGTT
5041    ---------+---------+---------+---------+---------+---------+ 5100
        AGGGTAGAGATGTTTTTATTTTAATTGTTGGACCATACCACCGTATCTGACAAGGGTCAA

ACTTAGGAGGCTCAGCGGGGAGGACTGTTTATGCAAATAGGAAGCTGCAATGAGCCCTGA
5101    ---------+---------+---------+---------+---------+---------+ 5160
        TGAATCCTCCGAGTCGCCCCTCCTGACAAATACGTTTATCCTTCGACGTTACTCGGGACT

TGATCCTGCTGCTGCACTCCAGCCTGGGCAACACAGCAAAACCATCTCTACGAAAAAAAA
5161    ---------+---------+---------+---------+---------+---------+ 5220
        ACTAGGACGACGACGTGAGGTCGGACCCGTTGTGTCGTTTTGGTAGAGATGCTTTTTTTT

AGTTCCCACTGACTGGCAAGGAAAGCCAGGAAGGGGGGCTCAGGTGCCCTCTCAGCCATG
5221    ---------+---------+---------+---------+---------+---------+ 5280
        TCAAGGGTGACTGACCGTTCCTTTCGGTCCTTCCCCCGAGTCCACGGGAGAGTCGGTAC

TACCTGTTCTTCTGGAAGGGCCTCCTCGCTTCTGCCAGGCTCATCACATCTTTTTTTTTT
5281    ---------+---------+---------+---------+---------+---------+ 5340
        ATGGACAAGAAGACCTTCCCGGAGGAGCGAAGACGGTCCGAGTAGTGTAGAAAAAAAAAA
```

Figure 1 – page 8

```
      TTGAGACAGAGTCTTGCTCTGTCACCCTGGCTGGAGTGCAGTGGCATGATCTCAGCTCAC
5341  ---------+---------+---------+---------+---------+---------+  5400
      AACTCTGTCTCAGAACGAGACAGTGGGACCGACCTCACGTCACCGTACTAGAGTCGAGTG

TGCAACCTCCGCCTCCCCAGTTCAAGTGATTCTCCTGCCTCAGCCTCCTGAGTAGCTGGG
5401  ---------+---------+---------+---------+---------+---------+  5460
      ACGTTGGAGGCGGAGGGGTCAAGTTCACTAAGAGGACGGAGTCGGAGGACTCATCGACCC

ATTACAGGCGTGTGCTACCACACCCGGCTAATTTTTGTATTCTTTTTAGTAGAGACGGGG
5461  ---------+---------+---------+---------+---------+---------+  5520
      TAATGTCCGCACACGATGGTGTGGGCCGATTAAAAACATAAGAAAAATCATCTCTGCCCC

TTTCACCATGTTGGTCAAGTGGATCTCAAACTCTTGACCTTGTGATCCTCCTGCCTCGAC
5521  ---------+---------+---------+---------+---------+---------+  5580
      AAAGTGGTACAACCAGTTCACCTAGAGTTTGAGAACTGGAACACTAGGAGGACGGAGCTG

CTCACAAAGTGCTGGAATTACAGGCGTGAGCCACCGCGCCTGGCCCTTTTTTTTTTTGAG
5581  ---------+---------+---------+---------+---------+---------+  5640
      GAGTGTTTCACGACCTTAATGTCCGCACTCGGTGGCGCGGACCGGGAAAAAAAAAAACTC

ACAGTTTCACTCTTGTTGCCGAGGCTAGAGCGCAATCGTGTGATCTCGGTTCACTGCAAC
5641  ---------+---------+---------+---------+---------+---------+  5700
      TGTCAAAGTGAGAACAACGGCTCCGATCTCGCGTTAGCACACTAGAGCCAAGTGACGTTG

CACCGCCTCCTGGGTTCAAGCAATTCTCCTGCTTCAGCCTCCCAAGGAGCTGGGATTACA
5701  ---------+---------+---------+---------+---------+---------+  5760
      GTGGCGGAGGACCCAAGTTCGTTAAGAGGACGAAGTCGGAGGGTTCCTCGACCCTAATGT

GGTACCTGCCACCACGCCCGGCTAATTTTGTATTTTTAGTAGAGATGGGGTTTCACCATG
5761  ---------+---------+---------+---------+---------+---------+  5820
      CCATGGACGGTGGTGCGGGCCGATTAAAACATAAAAATCATCTCTACCCCAAAGTGGTAC

TTGGTCAGGCTGGTCTTGAACTCCTGACCTCAGGTGATCTGGCACCTTGGCCTCCCAAAG
5821  ---------+---------+---------+---------+---------+---------+  5880
      AACCAGTCCGACCAGAACTTGAGGACTGGAGTCCACTAGACCGTGGAACCGGAGGGTTTC

TGCCGGGATTAGAGGCATGAGCCACCACGCCCAGCCTTCATCACATCTTGAGAGAGGACA
5881  ---------+---------+---------+---------+---------+---------+  5940
      ACGGCCCTAATCTCCGTACTCGGTGGTGCGGGTCGGAAGTAGTGTAGAACTCTCTCCTGT

CTGTCTGCCTCTTGCTCTGATGAGGGTCTGATGCAAAGGATAGTGAGTCTCTACAGTGCA
5941  ---------+---------+---------+---------+---------+---------+  6000
      GACAGACGGAGAACGAGACTACTCCCAGACTACGTTTCCTATCACTCAGAGATGTCACGT

CACTTAAGAAAGGCAGCATGTGGGTGCTCACAGGTCAGGCGGAGGAGGGGGAGCTGGTGG
6001  ---------+---------+---------+---------+---------+---------+  6060
      GTGAATTCTTTCCGTCGTACACCCACGAGTGTCCAGTCCGCCTCCTCCCCCTCGACCACC

GGACCAGGCATGCCTTGCTCCAGATCAGGATATGATGGCATTGGTGCAGATTATATTAGT
6061  ---------+---------+---------+---------+---------+---------+  6120
      CCTGGTCCGTACGGAACGAGGTCTAGTCCTATACTACCGTAACCACGTCTAATATAATCA
```

Figure 1 – page 9

```
         ATAGAATATGGTCTCAGGAACCAGGCAGGACTTTGGCTTCCGAGCAGGGTTCAGATCCCA
6121     ---------+---------+---------+---------+---------+---------+ 6180
         TATCTTATACCAGAGTCCTTGGTCCGTCCTGAAACCGAAGGCTCGTCCCAAGTCTAGGGT

GCTTGGCCCTACCTGTGCAGTGAGATCTCAAGCAAGTCAGCCTCTAAGCCTCAGGTTCCT
6181     ---------+---------+---------+---------+---------+---------+ 6240
         CGAACCGGGATGGACACGTCACTCTAGAGTTCGTTCAGTCGGAGATTCGGAGTCCAAGGA

G(I4(1369))A
         CCTTTGCCAGTTCAACAGATGAGCTGGCCTGGGGTGGGCTGTGTGGTGATGGTGCTGGGG
6241     ---------+---------+---------+---------+---------+---------+ 6300
         GGAAACGGTCAAGTTGTCTACTCGACCGGACCCCACCCGACACACCACTACCACGACCCC

EXON 5
         CTGGGTCCTCTGCCCCTGCAGGTGGTCTATGTTGCCCGAAACCCAAAGGACGTGGCGGTC
6301     ---------+---------+---------+---------+---------+---------+ 6360
         GACCCAGGAGACGGGGACGTCCACCAGATACAACGGGCTTTGGGTTTCCTGCACCGCCAG

TCCTACTACCATTTCCACCGTATGGAAAAGGCGCACCCTGAGCCTGGGACCTGGGACAGC
6361     ---------+---------+---------+---------+---------+---------+ 6420
         AGGATGATGGTAAAGGTGGCATACCTTTTCCGCGTGGGACTCGGACCCTGGACCCTGTCG

TTCCTGGAAAAGTTCATGGCTGGAGAAGGTGGGCTTGACTGGAGGAAGGAGGGTGTGAAG
6421     ---------+---------+---------+---------+---------+---------+ 6480
         AAGGACCTTTTCAAGTACCGACCTCTTCCACCCGAACTGACCTCCTTCCTCCCACACTTC

CCGAGGGGTGGTGGCTATAACGTACAGCAACCCTGTGTCGGTGCCCCCTGCCCGCTTCTC
6481     ---------+---------+---------+---------+---------+---------+ 6540
         GGCTCCCCACCACCGATATTGCATGTCGTTGGGACACAGCCACGGGGACGGGCGAAGAG

EXON 6
         TAGTGTCCTACGGGTCCTGGTACCAGCACGTGCAGGAGTGGTGGGAGCTGAGCCGCACCC
6541     ---------+---------+---------+---------+---------+---------+ 6600
         ATCACAGGATGCCCAGGACCATGGTCGTGCACGTCCTCACCACCCTCGACTCGGCGTGGG

ACCCTGTTCTCTACCTCTTCTATGAAGACATGAAGGAGGTGAGACCGACTGTGATGCTTC
6601     ---------+---------+---------+---------+---------+---------+ 6660
         TGGGACAAGAGATGGAGAAGATACTTCTGTACTTCCTCCACTCTGGCTGACACTACGAAG

CCCCCATGTGACACCTGGGGGCAGGCACCTCACAGGGACCCACCAAGGCCACCCAGCCCC
6661     ---------+---------+---------+---------+---------+---------+ 6720
         GGGGGTACACTGTGGACCCCCGTCCGTGGAGTGTCCCTGGGTGGTTCCGGTGGGTCGGGG

GTCCCTGGGCGGCTCCCACAGCAAGCCCGGATTCCCCATCCTACCTCCCTGGCCCAGGCC
6721     ---------+---------+---------+---------+---------+---------+ 6780
         CAGGGACCCGCCGAGGGTGTCGTTCGGGCCTAAGGGGTAGGATGGAGGGACCGGGTCCGG

CCCCCACTGCAGCCCCACCTGGCAGCAGGCTCGGCACAGCTTTCATCTTCTGCACCTGAG
6781     ---------+---------+---------+---------+---------+---------+ 6840
         GGGGGTGACGTCGGGGTGGACCGTCGTCCGAGCCGTGTCGAAAGTAGAAGACGTGGACTC
```

Figure 1 – page 10

```
           TCAGCTGCATGGGTGGCCACGGATCAGATACTTAGTCCTATTGCTTATCCTCACCAAAGG
6841    ---------+---------+---------+---------+---------+---------+  6900
           AGTCGACGTACCCACCGGTGCCTAGTCTATGAATCAGGATAACGAATAGGAGTGGTTTCC

GTGTGCCACCCAGGGCCACAGTCATGGAAGAAGACCATCCCGGTCCTCACCCATAGGCGC
6901    ---------+---------+---------+---------+---------+---------+  6960
           CACACGGTGGGTCCCGGTGTCAGTACCTTCTTCTGGTAGGGCCAGGAGTGGGTATCCGCG

CAAGCCCTGTTCATGATGGGATCACAGGGCAGAGATCAATTCATTTTACTCCAGAGACTA
6961    ---------+---------+---------+---------+---------+---------+  7020
           GTTCGGGACAAGTACTACCCTAGTGTCCCGTCTCTAGTTAAGTAAAATGAGGTCTCTGAT

GGGCCCCAGGGGTTGAGGCTCTTTGGGGTTTCTAGGGGAAGTGGCCAGATCCCCTCTGAG
7021    ---------+---------+---------+---------+---------+---------+  7080
           CCCGGGGTCCCCAACTCCGAGAAACCCCAAAGATCCCCTTCACCGGTCTAGGGGAGACTC

EXON 7
           GTTAGAGAGGGGGACCCGTTTTGTTTTGCTCCACTGAGGAGCCCTCTGCTGCTCAGAACC
7081    ---------+---------+---------+---------+---------+---------+  7140
           CAATCTCTCCCCCTGGGCAAAACAAAACGAGGTGACTCCTCGGGAGACGACGAGTCTTGG

CCAAAAGGGAGATTCAAAAGATCCTGGAGTTTGTGGGGCGCTCCCTGCCAGAGGAGACCA
7141    ---------+---------+---------+---------+---------+---------+  7200
           GGTTTTCCCTCTAAGTTTTCTAGGACCTCAAACACCCCGCGAGGGACGGTCTCCTCTGGT
                                                        G702T
           TGGACTTCATGGTTCAGCACACGTCGTTCAAGGAGATGAAGAAGAACCCTATGACCAACT
7201    ---------+---------+---------+---------+---------+---------+  7260
           ACCTGAAGTACCAAGTCGTGTGCAGCAAGTTCCTCTACTTCTTCTTGGGATACTGGTTGA

ACACCACCGTCCCCCAGGAGCTCATGGACCACAGCATCTCCCCCTTCATGAGGAAAGGTG
7261    ---------+---------+---------+---------+---------+---------+  7320
           TGTGGTGGCAGGGGGTCCTCGAGTACCTGGTGTCGTAGAGGGGGAAGTACTCCTTTCCAC

GGTGCTGGCCAGCACGGGGGTTTGGGGCGGGTGGGAGCAGCAGCTGCAGCCTCCCCATAG
7321    ---------+---------+---------+---------+---------+---------+  7380
           CCACGACCGGTCGTGCCCCCAAACCCCGCCCACCCTCGTCGTCGACGTCGGAGGGGTATC

EXON 8                                              C(I7(113))T
           GCACTTGGGGCCTCCCCTGGGATGAGACTCCAGCTTTGCTCCCTGCCTTCCTCCCCCAGG
7381    ---------+---------+---------+---------+---------+---------+  7440
           CGTGAACCCCGGAGGGGACCCTACTCTGAGGTCGAAACGAGGGACGGAAGGAGGGGGTCC

CATGGCTGGGGACTGGAAGACCACCTTCACCGTGGCGCAGAATGAGCGCTTCGATGCGGA
7441    ---------+---------+---------+---------+---------+---------+  7500
           GTACCGACCCCTGACCTTCTGGTGGAAGTGGCACCGCGTCTTACTCGCGAAGCTACGCCT

G843A
           CTATGCGGAGAAGATGGCAGGCTGCAGCCTCAGCTTCCGCTCTGAGCTGTGAGAGGGGCT
7501    ---------+---------+---------+---------+---------+---------+  7560
           GATACGCCTCTTCTACCGTCCGACGTCGGAGTCGAAGGCGAGACTCGACACTCTCCCCGA
```

Figure 1 – page 11

```
      CCTGGAGTCACTGCAGAGGGAGTGTGCGAATCTACCCTGACCAATGGGCTCAAGAATAAA
7561  ---------+---------+---------+---------+---------+---------+ 7620
      GGACCTCAGTGACGTCTCCCTCACACGCTTAGATGGGACTGGTTACCCGAGTTCTTATTT

GTATGATTTTGAGTCAGGCACAGTGGCTCATGTCTGCAATCCCAGCGATTTGGGAGGTT
7621  ---------+---------+---------+---------+---------+---------+ 7680
      CATACTAAAACTCAGTCCGTGTCACCGAGTACAGACGTTAGGGTCGCTAAACCCTCCAA

GAGCTGGTAGGATCACAATAGGCCACGAATTTGAGACCAGCCTGGTAAAATAGTGAGACC
7681  ---------+---------+---------+---------+---------+---------+ 7740
      CTCGACCATCCTAGTGTTATCCGGTGCTTAAACTCTGGTCGGACCATTTTATCACTCTGG

TCATCTCTACAAAGATGTAAAAAAATTAGCCACATGTGCTGGCACTTACCTGTAGTCCCA
7741  ---------+---------+---------+---------+---------+---------+ 7800
      AGTAGAGATGTTTCTACATTTTTTTAATCGGTGTACACGACCGTGAATGGACATCAGGGT

GCTACTTGGGAAGCAGAGGCTGGAGGATCATTTCAGCCCAGGAGGTTGTGGATACAGTGA
7801  ---------+---------+---------+---------+---------+---------+ 7860
      CGATGAACCCTTCGTCTCCGACCTCCTAGTAAAGTCGGGTCCTCCAACACCTATGTCACT

GTTATGACATGCCCATTCACTACAGCCTGGATGACAAGCAAGACCCTCCCTCCAAAGAAA
7861  ---------+---------+---------+---------+---------+---------+ 7920
      CAATACTGTACGGGTAAGTGATGTCGGACCTACTGTTCGTTCTGGGAGGGAGGTTTCTTT

ATAAAGCTCAATTAAAATAAAATATGATTTGTGTTCATGTAGAGCCTGTATTGGAAAGGA
7921  ---------+---------+---------+---------+---------+---------+ 7980
      TATTTCGAGTTAATTTTATTTTATACTAAACACAAGTACATCTCGGACATAACCTTTCCT

AGAGAAACTCTGAGCTGAAAGAGTGAATGCCCGGTGGGGCCACATATGGTCACCTCTCCC
7981  ---------+---------+---------+---------+---------+---------+ 8040
      TCTCTTTGAGACTCGACTTTCTCACTTACGGGCCACCCCGGTGTATACCAGTGGAGAGGG

CCAGCCTTCAGCTCCCCAGGTCACCATATCTGGGGAGGGGAGAAGGGTTTGGAGAAGTAA
8041  ---------+---------+---------+---------+---------+---------+ 8100
      GGTCGGAAGTCGAGGGGTCCAGTGGTATAGACCCCTCCCCTCTTCCCAAACCTCTTCATT

AACCCAGGAGATGTGTGGAGGGGGATGTCTGTTTAATCCCAGCACATCCTCTGCTGTCC
8101  ---------+---------+---------+---------+---------+---------+ 8160
      TTGGGTCCTCTACACACCTCCCCCCTACAGACAAATTAGGGTCGTGTAGGAGACGACAGG

TGCCCCAAGATGGTGGAGGACGTCGAGTCCGCCGGGCAGCGTCACTTTTTCTTGGGCTCC
8161  ---------+---------+---------+---------+---------+---------+ 8220
      ACGGGGTTCTACCACCTCCTGCAGCTCAGGCGGCCCGTCGCAGTGAAAAGAACCCGAGG

TTAGAAGCTACCAGGTACCTCTGGGCCACACTGAGATGAGGGGAGTAGCCGCCTGCATAG
8221  ---------+---------+---------+---------+---------+---------+ 8280
      AATCTTCGATGGTCCATGGAGACCCGGTGTGACTCTACTCCCCTCATCGGCGGACGTATC

GAGGTGTCTTCAAACAGGATAGTATAGTCCCTCCTGGGGGTTGTGGGGGTAGGTGGCCAA
8281  ---------+---------+---------+---------+---------+---------+ 8340
      CTCCACAGAAGTTTGTCCTATCATATCAGGGAGGACCCCCAACACCCCCATCCACCGGTT
```

Figure 1 – page 12

```
      GGAAGGGTAGAGGAGCAAGCCCCCGGGGCTGGTTGTCAACTCACTTTGTTGGCTGGAATT
8341  ---------+---------+---------+---------+---------+---------+  8400
      CCTTCCCATCTCCTCGTTCGGGGGCCCCGACCAACAGTTGAGTGAAACAACCGACCTTAA

GGTTGTAACTTGACCACCTCGGGCAGGATCCCACTGCTCATCCCCAA   (SEQ ID NO:1)
8401  ---------+---------+---------+---------+-------  8447
      CCAACATTGAACTGGTGGAGCCCGTCCTAGGGTGACGAGTAGGGGTT   (SEQ ID NO:2)
```

Figure 2A – page 1

```
       GTGACGGGGAGGCGGTGCCCGGGGCATCTCCGCGGCGGAACTCAGCCTGTGAGAAGTCAC
    1  ---------+---------+---------+---------+---------+---------+  60

TGCTTTGGGGAGACCTGATCTGGCTGTGCCAGATGGACACTGAGAAAGAAGTAGAAGACT
   61  ---------+---------+---------+---------+---------+---------+  120

CAGAATTAGAAGAGGAACATGGAGCTGATCCAGGACACCTCCCGCCCGCCACTGGAGTAC
  121  ---------+---------+---------+---------+---------+---------+  180

GTGAAGGGGGTCCCGCTCATCAAGTACTTTGCAGAGGCACTGGGGCCCCTGCAGAGCTTC
  181  ---------+---------+---------+---------+---------+---------+  240

CAAGCCCGACCTGATGACCTGCTCATCAACACCTACCCCAAGTCTGGCACCACCTGGGTG
  241  ---------+---------+---------+---------+---------+---------+  300

AGCCAGATACTGGACATGATCTACCAGGGCGGCGACCTAGAGAAGTGTAACCGGGCTCCC
  301  ---------+---------+---------+---------+---------+---------+  360

ATCTACGTACGGGTGCCCTTCCTTGAGGTCAATGATCCAGGGGAACCCTCAGGGCTGGAG
  361  ---------+---------+---------+---------+---------+---------+  420

ACTCTGAAAGACACACCGCCCCCACGGCTCATCAAGTCACACCTGCCCCTGGCTCTGCTC
  421  ---------+---------+---------+---------+---------+---------+  480

CCTCAGACTCTGTTGGATCAGAAGGTCAAGGTGGTCTATGTTGCCCGAAACCCAAAGGAC
  481  ---------+---------+---------+---------+---------+---------+  540

GTGGCGGTCTCCTACTACCATTTCCACCGTATGGAAAAGGCGCACCCTGAGCCTGGGACC
  541  ---------+---------+---------+---------+---------+---------+  600

TGGGACAGCTTCCTGGAAAAGTTCATGGCTGGAGAAGTGTCCTACGGGTCCTGGTACCAG
  601  ---------+---------+---------+---------+---------+---------+  660

CACGTGCAGGAGTGGTGGGAGCTGAGCCGCACCCACCCTGTTCTCTACCTCTTCTATGAA
  661  ---------+---------+---------+---------+---------+---------+  720

GACATGAAGGAGAACCCCAAAAGGGAGATTCAAAAGATCCTGGAGTTTGTGGGGCGCTCC
  721  ---------+---------+---------+---------+---------+---------+  780

CTGCCAGAGGAGACCATGGACTTCATGGTTCAGCACACGTCGTTCAAGGAGATGAAGAAG
  781  ---------+---------+---------+---------+---------+---------+  840

AACCCTATGACCAACTACACCACCGTCCCCCAGGAGCTCATGGACCACAGCATCTCCCCC
  841  ---------+---------+---------+---------+---------+---------+  900

TTCATGAGGAAAGGCATGGCTGGGGACTGGAAGACCACCTTCACCGTGGCGCAGAATGAG
  901  ---------+---------+---------+---------+---------+---------+  960

CGCTTCGATGCGGACTATGCGGAGAAGATGGCAGGCTGCAGCCTCAGCTTCCGCTCTGAG
  961  ---------+---------+---------+---------+---------+---------+  1020

CTGTGAGAGGGGCTCCTGGAGTCACTGCAGAGGGAGTGTGCGAATCTACCCTGACCAATG
 1021  ---------+---------+---------+---------+---------+---------+  1080
```

Figure 2A – page 2

```
       GGCTCAAGAATAAAGTATGATTTTTGAGTCAGGCACAGTGGCTCATGTCTGCAATCCCAG
1081   ---------+---------+---------+---------+---------+---------+ 1140

CGATTTGGGAGGTTGAGCTGGTAGGATCACAATAGGCCACGAATTTGAGACCAGCCTGGT
1141   ---------+---------+---------+---------+---------+---------+ 1200

AAAATAGTGAGACCTCATCTCTACAAAGATGTAAAAAAATTAGCCACATGTGCTGGCACT
1201   ---------+---------+---------+---------+---------+---------+ 1260

TACCTGTAGTCCCAGCTACTTGGGAAGCAGAGGCTGGAGGATCATTTCAGCCCAGGAGGT
1261   ---------+---------+---------+---------+---------+---------+ 1320

TGTGGATACAGTGAGTTATGACATGCCCATTCACTACAGCCTGGATGACAAGCAAGACCC
1321   ---------+---------+---------+---------+---------+---------+ 1380

TCCCTCCAAAGAAAATAAAGCTCAATTAAAAT    (SEQ ID NO:3)
1381   ---------+---------+---------+--  1412
```

Figure 2B

```
MetGluLeuIleGlnAspThrSerArgProProLeuGluTyrValLysGlyValProLeu
IleLysTyrPheAlaGluAlaLeuGlyProLeuGlnSerPheGlnAlaArgProAspAsp
LeuLeuIleAsnThrTyrProLysSerGlyThrThrTrpValSerGlnIleLeuAspMet
IleTyrGlnGlyGlyAspLeuGluLysCysAsnArgAlaProIleTyrValArgValPro
PheLeuGluValAsnAspProGlyGluProSerGlyLeuGluThrLeuLysAspThrPro
ProProArgLeuIleLysSerHisLeuProLeuAlaLeuLeuProGlnThrLeuLeuAsp
GlnLysValLysValValTyrValAlaArgAsnProLysAspValAlaValSerTyrTyr
HisPheHisArgMetGluLysAlaHisProGluProGlyThrTrpAspSerPheLeuGlu
LysPheMetAlaGlyGluValSerTyrGlySerTrpTyrGlnHisValGlnGluTrpTrp
GluLeuSerArgThrHisProValLeuTyrLeuPheTyrGluAspMetLysGluAsnPro
LysArgGluIleGlnLysIleLeuGluPheValGlyArgSerLeuProGluGluThrMet
AspPheMetValGlnHisThrSerPheLysGluMetLysLysAsnProMetThrAsnTyr
ThrThrValProGlnGluLeuMetAspHisSerIleSerProPheMetArgLysGlyMet
AlaGlyAspTrpLysThrThrPheThrValAlaGlnAsnGluArgPheAspAlaAspTyr
AlaGluLysMetAlaGlyCysSerLeuSerPheArgSerGluLeu    (SEQ ID NO:4)
```

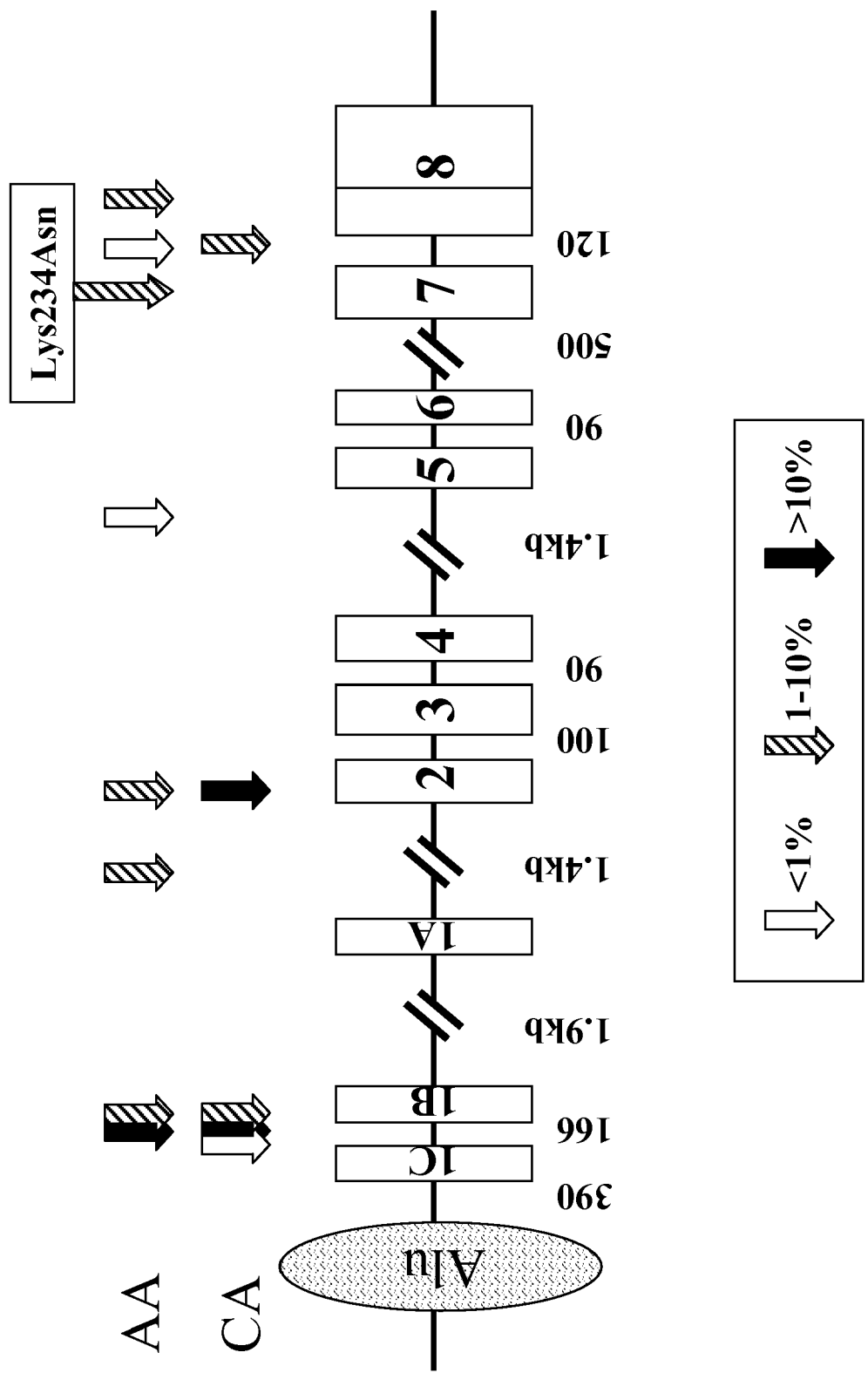

```
                              SEQUENCE LISTING

<160> NUMBER OF SEQ ID NOS: 18

<210> SEQ ID NO 1
<211> LENGTH: 8447
<212> TYPE: DNA
<213> ORGANISM: Homo sapiens

<400> SEQUENCE: 1
acctctgcct cctggttcca agcaatcctc cttcctcacc ctccagagta gctgggatta      60
cacgcgcctg ccaccgcgcc tggcctaatt tttgtatttt tagtagagat gggggtttcc     120
aaccatgttg gccaggctgg tctccaaact cctgacctca ggtgatcctg cccacctaag     180
cctcccaaaa tgctggtatt acaggcatga gccaccgtgc ccggcctaaa taattaataa     240
aataatggac gatgggtgcc ttctactgag ctcccggtaa ttgtgagtga gtagaggact     300
tgccctgggg acattcagtg acctgctggg tgttgctgag ctgtgaggaa gttcaggtct     360
ggctgcagtg gtgaggctgt gactcaatca atcactgctg atgctcccag gacctgcacc     420
agcttagtcc taggggcaag gattttaact gtccacctca gtttcttcat ttgtaagatg     480
caaataacag tcaccctgc ctcatgggat ggagctgtgt aatgcccgca acagtgcctg      540
ctgcatagag gggttgctgc cagctgcctc tccctccttg tctcttacct gcctgctgcc     600
tgggtcagga tgaagagggg cccttgtgtt gcccccaccc tggctgcctg ctaagggccc     660
atgtgatctg cctggcagag gagtttcttc aggaagaacc agggcagctt ctgcccctag     720
agggccaatg cccttggtga gtgcagtccc ctggcccag cctggtccac ctctgggaag      780
agggtgccca gttgtgcaat ccaggcccag gcagctgagc cctcatctca gcatgcaggg     840
cggatactgg aggggcttg tggcatctga ctctgtatct cctacctgcc cctctccttg      900
gtagctgtga gaagtcactg ctttggggag acctgatctg gctgtgccag atggacactg     960
agaaagaagt agaagactca gaattagaag aggtgagtgg gctttggtgg cgggctccct    1020 acccactcc ctgccctggg ctgcctgtga ccacactgct tgcctctgca ggcacactgg     1080
acagacctgc tggagacctg atcctcagtg tccttacccc ctcctacctc ttttctgtgc    1140
cacctgctgt gggtccagca ggtttttact tgagtacaat aaaaagtctg agtcaagggt    1200
gccttatggt ggatgctgag gggaggggcg gagctagtag cccaaggtcc tgccagtcac    1260
ggggcttcct caggggcaca gaggaggcag gaggggcccc tggccctagc acgtgaacag    1320
cttctactct gcctggaaac cccatgcctc agctttccc tacttgcctc tgagctcatg     1380
caattcttgg aagcctggga gacttacctt gaaattgaat gcaaatagga caaagaccaa    1440
ggaggatggg gggatgccct ccttccacgg ggccctgtgg cttccaagtc ttaatctcct    1500
ctagtctctt gtctacggag cctccttcaa acccagggaa agaaaagcac ctgccagggt    1560
tgtttttctt ctaggatctt ctattgatgc tctgtgaggt cccccaggag ccatgaagct    1620
agggctggct cctagggcaa tgggactaca gtgtccttgt cctttcttat tctttctgtt    1680
ctttctttct ttcttttttt tttttttttt ttttttgag acagagtctc actctgttgc     1740
ccaggctgga gtgcagtggt gtgatcttgg ctcactgaaa cctccgcctc ctgggttcaa    1800
gtgattctct tgcctcagcc tcctgagtag ctaggattac aggtgcccgc catcatgccc    1860
```

```
agctaattttt tgtattttta gtagagacag ggtttcacca tgttggccag cttggtctcg    1920
aactcctgac ctcaggtgat cctgctgcat cgacctccca aagtactggg attacaggcg    1980
tgagccacca cgctcagcct ctttcttgtt ctatatgtcc atgctctgct ccacttctgc    2040
cccttcactc tgccccacac atcactccag actggccttg tggtcagagc ctggaatgcc    2100
tgggctgctg ggggcctgtg gactgcactg ggccagaacc cctgccgcct tcaagactgg    2160
cctgtagcca gcaggtaggt gacttttccc aggccggcct atcccacctt tccctccac    2220 tcactcacct cccttgcctg ggtcaattag agaaagcttg tcggccaggc atggtggctc    2280
atgcctgtaa tctcagcact tgggaggcc gaggcgggcg gatcatctga gctcaggagt    2340
ttgagaccag cctggccaac atggcaaaac cccgtctcta ctaaaaatac aaaaattaac    2400
cggatgtggt ggtgtgcacc tgtaatccca gctactcggg aggctgaggc agaagaatcg    2460
cttgaaccca ggaggggag gttacagtga gcggagatcg tgctactgca ttgcagcctg    2520
ggcgagagag cgagtctcca tctcacataa aaaaagaaa aagaaagaaa gcaagcttgt    2580
ctgttggcct gccctgcagg gtggagttca gagggaaggt caggagccta gtgacagctc    2640
aaaaaaaaaa aacccaaat accaatgttg gccccttttg cctttcattc atgtgttttc    2700
tatacactaa actcacatat tgggtttgca gatcactcca agcttggctg gagctgtggt    2760
ggtaaggagg gtaatagaga agcttcccca ccctcaaccc caccccttcc ttcctggagt    2820
tcccagccct gactttagat ccctcccaca ctggaccttc aaaaccctca gggcagagag    2880
cagccctaca ctccctacac cacacccata ctcagcccct gcaggcaagg agagaacagg    2940
tcaggttccc gagagctcag gtgagtgaca cgttggaatg gcccagggca ccttcaccct    3000
gctcagcttg tggctccaac attctagaag ccgaggcctc tgccatccct gccctttccc    3060
atggatattc catttcaatt agacaaccca gcctggccgg aatcccctg cgttccttct    3120 tttcctttgt gtattttga cagggtgt tgctccgtca cccaggctgg agtgtagtgg    3180
gatcctggcc cactgcagcc tcaaattcct aggctgaggc aatcctgccg cctcagcctc    3240
ctgagtagct ggggttacaa gagcaagcca ccacacccag ctaattttga aaatattttt    3300
ttgtagagga gaggtcttgc tttgttgtcc aggttggtct caaactccag ggctcaaggg    3360
atcctttccc gttggcctcc caaggctctg ggattacagg cgggagtcac cctgcctggg    3420
cccctccttt tgatgagtca tcagttttca ttcccgcacg aggctctagc ccctggtacc    3480
agcttagttg ctcaatgggc tgtgtttgtt ctggagccca gatggactgt ggccaggcaa    3540
gtggatcaca gacctggccg gcctgggagg tttccacatg tgagggcat gagggggct    3600 caaggagggg agcatcgggg agaggagcgc actgggtgga ggctggggt cccagcagga    3660 aatggtgaga caaagggcgc tggctggcag ggagacagca caggcaggcc ctagagcttc    3720
ctcagcacag ctggactctc ctggagacct tcacacaccc tgatatctgg ccccgcgct    3780 acgagggtgc tttcactggt ctgcactatg ccccaggccc tgggattttg aacagctctg    3840
caggtgactg aaaggtgcgg ccaggctggg gaacgacctg gtttcagccc cagccccgcc    3900
actgactgac tttgtgagtg cgggcaagtc actcagcctc cctaggcctc agtgacttcc    3960
ctgaaagcaa aaactctgca aaggggcagc tgggtgctgg ctcacacctg taatcccagc    4020
actttgggag gctgaggtag acaaatcact tgaggccagg agttctagac cagcctggcc    4080
aacatggtga aaccccatct ctactaaaga aaaaaaaaa ttagctgagc atggttgtac    4140
atgcttgtaa tcccagctac ttgggatgcc gaggcgggag gattgcttga acccaagagg    4200
```

```
tggagtttgc agtgagctga gattgtgcca cactgcactc cagcttgggt gagagtgaga    4260
ctccatctca aaaaaaaaaa aaaaaagaga gaatcccact ttcttgctgt tgtgatggtg    4320
gtaagggaac gggcctggct ctggcccctg atgcaggaac atggagctga tccaggacac    4380
ctcccgcccg ccactggagt acgtgaaggg ggtcccgctc atcaagtact ttgcagaggc    4440 actgggccc  ctgcagagct tccaagcccg acctgatgac ctgctcatca acacctaccc    4500
caagtctggt aagtgaggag ggccacccac cctctcccag gcggcagtcc ccaccttggt    4560
cagcaaggtc gtgccctcag cctgctcacc tcctatctcc ctccctctcc aggcaccacc    4620
tgggtgagcc agatactgga catgatctac cagggcggcg acctagagaa gtgtaaccgg    4680
gctcccatct acgtacgggt gcccttcctt gaggtcaatg atccagggga accctcaggt    4740
gcatggctgg gtcctggggg taagggaagt ggaggaagac agggctgggg cttcagctca    4800
ccagaccttc cctgacccac tactcagggc tggagactct gaaagacaca ccgcccccac    4860
ggctcatcaa gtcacacctg ccctggctc  tgctccctca gactctgttg gatcagaagg    4920
tcaaggtgag gccggcctca atggttcaca cctgtcatcc cagtttgaga ctgaggaggg    4980
aggatccctt gaaggcgaga gatggagacc agcctgggca acattgctgt agagatgaca    5040
tcccatctct acaaaaataa aattaacaac ctggtatggt ggcatagact gttcccagtt    5100
acttaggagg ctcagcgggg aggactgttt atgcaaatag gaagctgcaa tgagccctga    5160
tgatcctgct gctgcactcc agcctgggca acacagcaaa accatctcta cgaaaaaaaa    5220
agttcccact gactggcaag gaaagccagg aaggggggct caggtgccct ctcagccatg    5280
tacctgttct tctggaaggg cctcctcgct tctgccaggc tcatcacatc ttttttttt    5340 ttgagacaga gtcttgctct gtcacccctgg ctggagtgca gtggcatgat ctcagctcac    5400
tgcaacctcc gcctcccag  ttcaagtgat tctcctgcct cagcctcctg agtagctggg    5460
attacaggcg tgtgctacca cacccggcta atttttgtat tcttttttagt agagacgggg    5520 tttcaccatg ttggtcaagt ggatctcaaa ctcttgacct tgtgatcctc ctgcctcgac    5580
ctcacaaagt gctggaatta caggcgtgag ccaccgcgcc tggccctttt tttttttgag    5640
acagtttcac tcttgttgcc gaggctagag cgcaatcgtg tgatctcggt tcactgcaac    5700
caccgcctcc tgggttcaag caattctcct gcttcagcct cccaaggagc tgggattaca    5760
ggtacctgcc accacgcccg gctaattttg tattttagt agagatgggg tttcaccatg    5820
ttggtcaggc tggtcttgaa ctcctgacct caggtgatct ggcaccttgg cctcccaaag    5880
tgccgggatt agaggcatga gccaccacgc ccagccttca tcacatcttg agagaggaca    5940
ctgtctgcct cttgctctga tgagggtctg atgcaaagga tagtgagtct ctacagtgca    6000
cacttaagaa aggcagcatg tgggtgctca caggtcaggc ggaggagggg gagctggtgg    6060
ggaccaggca tgccttgctc cagatcagga tatgatggca ttggtgcaga ttatattagt    6120
atagaatatg gtctcaggaa ccaggcagga cttttggcttc cgagcagggt tcagatccca    6180
gcttggccct acctgtgcag tgagatctca agcaagtcag cctctaagcc tcaggttcct    6240
cctttgccag ttcaacagat gagctggcct ggggtgggct gtgtggtgat ggtgctgggg    6300
ctgggtcctc tgcccctgca ggtggtctat gttgcccgaa acccaaagga cgtggcggtc    6360
tcctactacc atttccaccg tatggaaaag gcgcaccctg agcctgggac ctgggacagc    6420
ttcctggaaa agttcatggc tggagaaggt gggcttgact ggaggaagga gggtgtgaag    6480
ccgaggggtg gtggctataa cgtacagcaa ccctgtgtcg gtgccccctg cccgcttctc    6540
tagtgtccta cgggtcctgg taccagcacg tgcaggagtg gtgggagctg agccgcaccc    6600
```

```
acctgttct ctacctcttc tatgaagaca tgaaggaggt gagaccgact gtgatgcttc    6660 ccccatgtg acacctgggg gcaggcacct cacagggacc caccaaggcc acccagcccc    6720
gtccctgggc ggctcccaca gcaagcccgg attccccatc ctacctccct ggcccaggcc    6780
cccccactgc agccccacct ggcagcaggc tcggcacagc tttcatcttc tgcacctgag    6840
tcagctgcat gggtggccac ggatcagata cttagtccta ttgcttatcc tcaccaaagg    6900
gtgtgccacc cagggccaca gtcatggaag aagaccatcc cggtcctcac ccataggcgc    6960
caagccctgt tcatgatggg atcacagggc agagatcaat tcattttact ccagagacta    7020 gggcccagg ggttgaggct ctttggggtt tctagggaa gtggccagat cccctctgag    7080
gttagagagg gggacccgtt ttgttttgct ccactgagga gccctctgct gctcagaacc    7140
ccaaaaggga gattcaaaag atcctggagt ttgtggggcg ctccctgcca gaggagacca    7200
tggacttcat ggttcagcac acgtcgttca aggagatgaa gaagaaccct atgaccaact    7260
acaccaccgt cccccaggag ctcatggacc acagcatctc ccccttcatg aggaaaggtg    7320
ggtgctggcc agcacggggg tttggggcgg gtgggagcag cagctgcagc ctccccatag    7380
gcacttgggg cctcccctgg gatgagactc cagctttgct ccctgccttc ctcccccagg    7440
catggctggg gactgaagga ccaccttcac cgtggcgcag aatgagcgct tcgatgcgga    7500
ctatgcggag aagatggcag gctgcagcct cagcttccgc tctgagctgt gagaggggct    7560
cctggagtca ctgcagaggg agtgtgcgaa tctaccctga ccaatgggct caagaataaa    7620
gtatgatttt tgagtcaggc acagtggctc atgtctgcaa tcccagcgat ttgggaggtt    7680
gagctggtag gatcacaata ggccacgaat ttgagaccag cctggtaaaa tagtgagacc    7740
tcatctctac aaagatgtaa aaaaattagc cacatgtgct ggcacttacc tgtagtccca    7800
gctacttggg aagcagaggc tggaggatca tttcagccca ggaggttgtg gatacagtga    7860
gttatgacat gcccattcac tacagcctgg atgacaagca agaccctccc tccaaagaaa    7920
ataaagctca attaaaataa aatatgattt gtgttcatgt agagcctgta ttggaaagga    7980
agagaaactc tgagctgaaa gagtgaatgc ccggtgggc cacatatggt cacctctccc    8040
ccagccttca gctcccccagg tcaccatatc tggggagggg agaagggttt ggagaagtaa    8100 aaccaggag atgtgtggag gggggatgtc tgtttaatcc cagcacatcc tctgctgtcc    8160
tgccccaaga tggtggagga cgtcgagtcc gccgggcagc gtcacttttt cttgggctcc    8220
ttagaagcta ccaggtacct ctgggccaca ctgagatgag gggagtagcc gcctgcatag    8280
gaggtgtctt caaacaggat agtatagtcc ctcctggggg ttgtgggggt aggtggccaa    8340
ggaagggtag aggagcaagc ccccgggct ggttgtcaac tcactttgtt ggctggaatt    8400
ggttgtaact tgaccacctc gggcaggatc ccactgctca tccccaa    8447
```

<210> SEQ ID NO 2
<211> LENGTH: 8447
<212> TYPE: DNA
<213> ORGANISM: Homo sapiens

<400> SEQUENCE: 2

```
ttggggatga gcagtgggat cctgcccgag gtggtcaagt tacaaccaat tccagccaac      60
aaagtgagtt gacaaccagc cccgggggct tgctcctcta cccttccttg gccacctacc     120
cccacaaccc ccaggaggga ctatactatc ctgtttgaag acacctccta tgcaggcggc     180 tactccccctc atctcagtgt ggcccagagg tacctggtag cttctaagga gcccaagaaa     240
```

-continued

```
aagtgacgct gcccggcgga ctcgacgtcc tccaccatct tggggcagga cagcagagga    300
tgtgctggga ttaaacagac atccccctc cacacatctc ctgggtttta cttctccaaa    360
cccttctccc ctcccagat atggtgacct ggggagctga aggctggggg agaggtgacc    420
atatgtggcc ccaccgggca ttcactcttt cagctcagag tttctcttcc tttccaatac    480
aggctctaca tgaacacaaa tcatatttta ttttaattga gctttatttt ctttggaggg    540
agggtcttgc ttgtcatcca ggctgtagtg aatgggcatg tcataactca ctgtatccac    600
aacctcctgg gctgaaatga tcctccagcc tctgcttccc aagtagctgg gactacaggt    660
aagtgccagc acatgtggct aattttttta catctttgta gagatgaggt ctcactattt    720
taccaggctg gtctcaaatt cgtggcctat tgtgatccta ccagctcaac ctcccaaatc    780
gctgggattg cagacatgag ccactgtgcc tgactcaaaa atcatacttt attcttgagc    840
ccattggtca gggtagattc gcacactccc tctgcagtga ctccaggagc ccctctcaca    900
gctcagagcg gaagctgagg ctgcagcctg ccatcttctc cgcatagtcc gcatcgaagc    960
gctcattctg cgccacggtg aaggtggtct tccagtcccc agccatgcct gggggaggaa   1020
ggcagggagc aaagctggag tctcatccca ggggaggccc caagtgccta tggggaggct   1080
gcagctgctg ctcccacccg ccccaaaccc ccgtgctggc cagcacccac ctttcctcat   1140 gaaggggag atgctgtggt ccatgagctc ctggggacg gtggtgtagt tggtcatagg    1200
gttcttcttc atctccttga acgacgtgtg ctgaaccatg aagtccatgg tctcctctgg   1260
cagggagcgc cccacaaact ccaggatctt ttgaatctcc cttttgggt tctgagcagc    1320 agagggctcc tcagtggagc aaaacaaaac gggtccccct ctctaacctc agagggatc    1380 tggccacttc ccctagaaac cccaaagagc ctcaacccct ggggccctag tctctggagt   1440
aaaatgaatt gatctctgcc ctgtgatccc atcatgaaca gggcttggcg cctatgggtg    1500
aggaccggga tggtcttctt ccatgactgt ggccctgggt ggcacaccct ttggtgagga   1560
taagcaatag gactaagtat ctgatccgtg gccacccatg cagctgactc aggtgcagaa   1620
gatgaaagct gtgccgagcc tgctgccagg tggggctgca gtgggggggc ctgggccagg   1680
gaggtaggat ggggaatccg ggcttgctgt gggagccgcc cagggacggg gctgggtggc   1740
cttggtgggt ccctgtgagg tgcctgcccc caggtgtcac atggggggaa gcatcacagt   1800
cggtctcacc tccttcatgt cttcatagaa gaggtagaga acagggtggg tgcggctcag   1860
ctcccaccac tcctgcacgt gctggtacca ggacccgtag gacactagag aagcgggcag   1920
ggggcaccga cacagggttg ctgtacgtta tagccaccac ccctcggctt cacaccctcc   1980
ttcctccagt caagcccacc ttctccagcc atgaactttt ccaggaagct gtcccaggtc   2040
ccaggctcag ggtgcgcctt ttccatacgg tggaaatggt agtaggagac cgccacgtcc   2100
tttgggtttc gggcaacata gaccacctgc aggggcagag gacccagccc cagcaccatc   2160
accacacagc ccaccccagg ccagctcatc tgttgaactg gcaaaggagg aacctgaggc   2220
ttagaggctg acttgcttga gatctcactg cacaggtagg gccaagctgg gatctgaacc   2280
ctgctcggaa gccaaagtcc tgcctggttc ctgagaccat attctatact aatataatct   2340
gcaccaatgc catcatatcc tgatctggag caaggcatgc ctggtcccca ccagctcccc   2400
ctcctccgcc tgacctgtga gcaccacat gctgcctttc ttaagtgtgc actgtagaga    2460
ctcactatcc tttgcatcag accctcatca gagcaagagg cagacagtgt cctctctcaa   2520
gatgtgatga aggctgggcg tggtggctca tgcctctaat cccggcactt tgggaggcca   2580
aggtgccaga tcacctgagg tcaggagttc aagaccagcc tgaccaacat ggtgaaaccc   2640
```

```
catctctact aaaaatacaa aattagccgg gcgtggtggc aggtacctgt aatcccagct   2700
ccttgggagg ctgaagcagg agaattgctt gaacccagga ggcggtggtt gcagtgaacc   2760
gagatcacac gattgcgctc tagcctcggc aacaagagtg aaactgtctc aaaaaaaaaa   2820
agggccaggc gcggtggctc acgcctgtaa ttccagcact ttgtgaggtc gaggcaggag   2880
gatcacaagg tcaagagttt gagatccact gaccaacat ggtgaaaccc cgtctctact    2940
aaaaagaata caaaaattag ccgggtgtgg tagcacacgc ctgtaatccc agctactcag   3000
gaggctgagg caggagaatc acttgaactg gggaggcgga ggttgcagtg agctgagatc   3060
atgccactgc actccagcca gggtgacaga gcaagactct gtctcaaaaa aaaaaagat    3120 gtgatgagcc tggcagaagc gaggaggccc ttccagaaga acaggtacat ggctgagagg   3180
gcacctgagc cccccttcct ggctttcctt gccagtcagt gggaactttt ttttcgtag    3240 agatggtttt gctgtgttgc ccaggctgga gtgcagcagc aggatcatca gggctcattg   3300
cagcttccta tttgcataaa cagtcctccc cgctgagcct cctaagtaac tgggaacagt   3360
ctatgccacc ataccaggtt gttaatttta ttttgtaga gatgggatgt catctctaca    3420
gcaatgttgc ccaggctggt ctccatctct cgccttcaag ggatcctccc tcctcagtct   3480
caaactggga tgacaggtgt gaaccattga ggccggcctc accttgacct tctgatccaa   3540
cagagtctga gggagcagag ccaggggcag gtgtgacttg atgagccgtg ggggcggtgt   3600
gtctttcaga gtctccagcc ctgagtagtg ggtcagggaa ggtctggtga gctgaagccc   3660
cagccctgtc ttcctccact tcccttaccc ccaggaccca gccatgcacc tgagggttcc   3720
cctggatcat tgacctcaag gaagggcacc cgtacgtaga tgggagcccg gttacacttc   3780
tctaggtcgc cgccctggta gatcatgtcc agtatctggc tcacccaggt ggtgcctgga   3840
gagggaggga gataggaggt gagcaggctg agggcacgac cttgctgacc aaggtgggga   3900
ctgccgcctg ggagagggtg ggtggccctc ctcacttacc agacttgggg taggtgttga   3960
tgagcaggtc atcaggtcgg gcttggaagc tctgcagggg ccccagtgcc tctgcaaagt   4020
acttgatgag cggacccccc ttcacgtact ccagtggcgg gcgggaggtg tcctggatca   4080
gctccatgtt cctgcatcag gggccagagc caggcccgtt cccttaccac catcacaaca   4140
gcaagaaagt gggattctct cttttttttt tttttttga gatggagtct cactctcacc   4200
caagctggag tgcagtgtgg cacaatctca gctcactgca aactccacct cttgggttca   4260
agcaatcctc ccgcctcggc atcccaagta gctgggatta caagcatgta caaccatgct   4320
cagctaattt ttttttttct ttagtagaga tgggggttca ccatgttggc caggctggtc   4380
tagaactcct ggcctcaagt gatttgtcta cctcagcctc ccaaagtgct gggattacag   4440
gtgtgagcca gcacccagct gccccttgc agagttttg ctttcaggga agtcactgag    4500
gcctagggag gctgagtgac ttgcccgcac tcacaaagtc agtcagtggc ggggctgggg   4560
ctgaaaccag gtcgttcccc agcctggccg cacctttcag tcacctgcag agctgttcaa   4620
aatcccaggg cctggggcat agtgcagacc agtgaaagca ccctcgtagc gcggggccca   4680
gatatcaggg tgtgtgaagg tctccaggag agtccagctg tgctgaggaa gctctagggc   4740
ctgcctgtgc tgtctcctg ccagccagcg ccctttgtct caccatttcc tgctgggacc    4800
cccagcctcc acccagtgcg ctcctctccc cgatgctccc ctccttgagc cccctcatg    4860 cccctcacat gtggaaacct cccaggccgg ccaggtctgt gatccacttg cctggccaca   4920
gtccatctgg gctccagaac aaacacagcc cattgagcaa ctaagctggt accaggggct   4980
```

```
agagcctcgt gcgggaatga aaactgatga ctcatcaaaa ggaggggccc aggcagggtg    5040
actcccgcct gtaatcccag agccttggga ggccaacggg aaaggatccc ttgagccctg    5100
gagtttgaga ccaacctgga caacaaagca agacctctcc tctacaaaaa atattttttca   5160 aaattagctg ggtgtggtgg cttgctcttg taacccagc tactcaggag gctgaggcgg     5220
caggattgcc tcagcctagg aatttgaggc tgcagtgggc caggatccca ctacactcca    5280
gcctgggtga cggagcaaca ccctgtctca aaaatacaca aaggaaaaga aggaacgcag    5340
ggggattccg gccaggctgg gttgtctaat tgaaatggaa tatccatggg aaagggcagg    5400
gatggcagag gcctcggctt ctagaatgtt ggagccacaa gctgagcagg gtgaaggtgc    5460
cctgggccat tccaacgtgt cactcacctg agctctcggg aacctgacct gttctctcct    5520
tgcctgcagg ggctgagtat gggtgtggtg tagggagtgt agggctgctc tctgccctga    5580
gggttttgaa ggtccagtgt gggagggatc taaagtcagg gctgggaact ccaggaagga    5640
aggggtgggg ttgagggtgg ggaagcttct ctattaccct ccttaccacc acagctccag    5700
ccaagcttgg agtgatctgc aaacccaata tgtgagttta gtgtatagaa acacatgaa     5760 tgaaaggcaa aagggggccaa cattggtatt tgggttttttt ttttttttgag ctgtcactag  5820 gctcctgacc ttccctctga actccaccct gcagggcagg ccaacagaca agcttgcttt    5880 cttttcttttt cttttttttta tgtgagatgg agactcgctc tctcgcccag gctgcaatgc   5940
agtagcacga tctccgctca ctgtaacctc cccctcctgg gttcaagcga ttcttctgcc    6000
tcagcctccc gagtagctgg gattacaggt gcacaccacc acatccggtt aattttttgta   6060 ttttttagtag agacggggtt ttgccatgtt ggccaggctg gtctcaaact cctgagctca    6120
gatgatccgc ccgcctcggc ctcccaaagt gctgagatta caggcatgag ccaccatgcc    6180
tggccgacaa gctttctcta attgacccag gcaagggagg tgagtgagtg gaggggaaag    6240
gtgggatagg ccggcctggg aaaagtcacc tacctgctgg ctacaggcca gtcttgaagg    6300 cggcagggt tctggcccag tgcagtccac aggcccccag cagcccaggc attccaggct     6360
ctgaccacaa ggccagtctg gagtgatgtg tggggcagag tgaaggggca gaagtggagc    6420
agagcatgga catatagaac aagaaagagg ctgagcgtgg tggctcacgc ctgtaatccc    6480
agtactttgg gaggtcgatg cagcaggatc acctgaggtc aggagttcga gaccaagctg    6540
gccaacatgg tgaaaccctg tctctactaa aaatacaaaa attagctggg catgatggcg    6600
ggcacctgta atcctagcta ctcaggaggc tgaggcaaga gaatcacttg aacccaggag    6660
gcggaggttt cagtgagcca agatcacacc actgcactcc agcctgggca acagagtgag    6720
actctgtctc aaaaaaaaaa aaaaaaaaaa aaagaaaga agaaagaac agaaagaata      6780 agaaaggaca aggacactgt agtcccattg ccctaggagc cagccctagc ttcatggctc    6840
ctgggggacc tcacagagca tcaatagaag atcctagaag aaaaacaacc ctggcaggtg    6900
cttttctttc cctgggtttg aaggaggctc cgtagacaag agactagagg agattaagac    6960
ttggaagcca cagggccccg tggaaggagg gcatccccc atcctccttg gtctttgtcc     7020
tatttgcatt caatttcaag gtaagtctcc caggcttcca agaattgcat gagctcgagg    7080
gcaagtaggg gaaagctgag gcatgggggtt tccaggcaga gtagaagctg ttcacgtgct   7140
agggccaggg gcccctcctg cctcctctgt gcccctgagg aagcccgtg actggcagga    7200 ccttgggcta ctagctccgc ccctcccctc agcatccacc ataaggcacc cttgactcag    7260 acttttttatt gtactcaagt aaaaacctgc tggacccaca gcaggtggca cagaaaagag    7320
gtaggagggg gtaaggacac tgaggatcag gtctccagca ggtctgtcca gtgtgcctgc    7380
```

```
agaggcaagc agtgtggtca caggcagccc agggcaggga gtggggtagg gagcccgcca    7440
ccaaagccca ctcacctctt ctaattctga gtcttctact tctttctcag tgtccatctg    7500
gcacagccag atcaggtctc cccaaagcag tgacttctca cagctaccaa ggagaggggc    7560
aggtaggaga tacagagtca gatgccacaa gcccctcca gtatccgccc tgcatgctga     7620
gatgagggct cagctgcctg gcctggatt gcacaactgg gcaccctctt cccagaggtg     7680
gaccaggctg gggccagggg actgcactca ccaagggcat tggccctcta ggggcagaag    7740 ctgcccctggt tcttcctgaa gaaactcctc tgccaggcag atcacatggg cccttagcag   7800
gcagccaggg tgggggcaac acaagggccc ctcttcatcc tgacccaggc agcaggcagg    7860
taagagacaa ggagggagag gcagctggca gcaaccccctc tatgcagcag gcactgttgc   7920
gggcattaca cagctccatc ccatgaggca ggggtgactg ttatttgcat cttacaaatg    7980
aagaaactga ggtggacagt taaaatcctt gccctagga ctaagctggt gcaggtcctg     8040
ggagcatcag cagtgattga ttgagtcaca gcctcaccac tgcagccaga cctgaacttc    8100
ctcacagctc agcaacaccc agcaggtcac tgaatgtccc cagggcaagt cctctactca   8160
ctcacaatta ccgggagctc agtagaaggc acccatcgtc cattattta ttaattattt     8220 aggccgggca cggtggctca tgcctgtaat accagcattt ggggaggctt aggtgggcag    8280
gatcacctga ggtcaggagt ttggagacca gcctggccaa catggttgga aacccccatc    8340
tctactaaaa atacaaaaat taggccaggc gcggtggcag gcgcgtgtaa tcccagctac    8400
tctggagggt gaggaaggag gattgcttgg aaccaggagg cagaggt                  8447

<210> SEQ ID NO 3
<211> LENGTH: 1412
<212> TYPE: DNA
<213> ORGANISM: Homo sapiens

<400> SEQUENCE: 3
gtgacgggga ggcggtgccc ggggcatctc cgcggcggaa ctcagcctgt gagaagtcac     60
tgctttgggg agacctgatc tggctgtgcc agatggacac tgagaaagaa gtagaagact    120
cagaattaga agaggaacat ggagctgatc caggacacct cccgcccgcc actggagtac    180 gtgaagggg tcccgctcat caagtacttt gcagaggcac tggggcccct gcagagcttc     240
caagcccgac ctgatgacct gctcatcaac acctacccca gtctggcac cacctgggtg     300 agccagatac tggacatgat ctaccagggc ggcgacctag agaagtgtaa ccgggctccc    360
atctacgtac gggtgcccctt ccttgaggtc aatgatccag gggaaccctc agggctggag   420
actctgaaag acacaccgcc cccacggctc atcaagtcac acctgcccct ggctctgctc    480
cctcagactc tgttggatca gaaggtcaag gtggtctatg ttgcccgaaa cccaaaggac    540
gtggcggtct cctactacca tttccaccgt atggaaaagg cgcaccctga gcctgggacc    600
tgggacagct tcctggaaaa gttcatggct ggagaagtgt cctacgggtc ctggtaccag    660
cacgtgcagg agtggtggga gctgagccgc acccaccctg ttctctacct cttctatgaa    720
gacatgaagg agaaccccaa aagggagatt caaaagatcc tggagtttgt ggggcgctcc    780
ctgccagagg agaccatgga cttcatggtt cagcacacgt cgttcaagga gatgaagaag    840
aaccctatga ccaactacac caccgtcccc caggagctca tggaccacag catctccccc    900
ttcatgagga aaggcatggc tggggactgg aagaccacct tcaccgtggc cagaatgag    960 cgcttcgatg cggactatgc ggagaagatg gcaggctgca gcctcagctt ccgctctgag   1020
```

-continued

```
ctgtgagagg ggctcctgga gtcactgcag agggagtgtg cgaatctacc ctgaccaatg    1080
ggctcaagaa taaagtatga tttttgagtc aggcacagtg gctcatgtct gcaatcccag    1140
cgatttggga ggttgagctg gtaggatcac aataggccac gaatttgaga ccagcctggt    1200
aaaatagtga gacctcatct ctacaaagat gtaaaaaaat tagccacatg tgctggcact    1260
tacctgtagt cccagctact tgggaagcag aggctggagg atcatttcag cccaggaggt    1320
tgtggataca gtgagttatg acatgccat tcactacagc ctggatgaca agcaagaccc    1380
tccctccaaa gaaataaag ctcaattaaa at                                   1412
```

<210> SEQ ID NO 4
<211> LENGTH: 295
<212> TYPE: PRT
<213> ORGANISM: Homo sapiens

<400> SEQUENCE: 4

```
Met Glu Leu Ile Gln Asp Thr Ser Arg Pro Leu Glu Tyr Val Lys
  1               5                  10                  15

Gly Val Pro Leu Ile Lys Tyr Phe Ala Glu Ala Leu Gly Pro Leu Gln
                 20                  25                  30

Ser Phe Gln Ala Arg Pro Asp Leu Leu Ile Asn Thr Tyr Pro Lys
             35                  40                  45

Ser Gly Thr Thr Trp Val Ser Gln Ile Leu Asp Met Ile Tyr Gln Gly
         50                  55                  60

Gly Asp Leu Glu Lys Cys Asn Arg Ala Pro Ile Tyr Val Arg Val Pro
 65                  70                  75                  80

Phe Leu Glu Val Asn Asp Pro Gly Glu Pro Ser Gly Leu Glu Thr Leu
                     85                  90                  95

Lys Asp Thr Pro Pro Arg Leu Ile Lys Ser His Leu Pro Leu Ala
                100                 105                 110

Leu Leu Pro Gln Thr Leu Leu Asp Gln Lys Val Lys Val Val Tyr Val
                115                 120                 125

Ala Arg Asn Pro Lys Asp Val Ala Val Ser Tyr Tyr His Phe His Arg
            130                 135                 140

Met Glu Lys Ala His Pro Glu Pro Gly Thr Trp Asp Ser Phe Leu Glu
145                 150                 155                 160

Lys Phe Met Ala Gly Glu Val Ser Tyr Gly Ser Trp Tyr Gln His Val
                    165                 170                 175

Gln Glu Trp Trp Glu Leu Ser Arg Thr His Pro Val Leu Tyr Leu Phe
                180                 185                 190

Tyr Glu Asp Met Lys Glu Asn Pro Lys Arg Glu Ile Gln Lys Ile Leu
            195                 200                 205

Glu Phe Val Gly Arg Ser Leu Pro Glu Glu Thr Met Asp Phe Met Val
        210                 215                 220

Gln His Thr Ser Phe Lys Glu Met Lys Lys Asn Pro Met Thr Asn Tyr
225                 230                 235                 240

Thr Thr Val Pro Gln Glu Leu Met Asp His Ser Ile Ser Pro Phe Met
                    245                 250                 255

Arg Lys Gly Met Ala Gly Asp Trp Lys Thr Thr Phe Thr Val Ala Gln
                260                 265                 270

Asn Glu Arg Phe Asp Ala Asp Tyr Ala Glu Lys Met Ala Gly Cys Ser
            275                 280                 285

Leu Ser Phe Arg Ser Glu Leu
        290                 295
```

<210> SEQ ID NO 5
<211> LENGTH: 43
<212> TYPE: DNA
<213> ORGANISM: Artificial Sequence
<220> FEATURE:
<223> OTHER INFORMATION: Primer

<400> SEQUENCE: 5
tgtaaaacga cggccagtta atggacgatg ggtgccttgt act                43

<210> SEQ ID NO 6
<211> LENGTH: 34
<212> TYPE: DNA
<213> ORGANISM: Artificial Sequence
<220> FEATURE:
<223> OTHER INFORMATION: Primer

<400> SEQUENCE: 6
caggaaacag ctatgaccat gggcccttag cagg                          34

<210> SEQ ID NO 7
<211> LENGTH: 38
<212> TYPE: DNA
<213> ORGANISM: Artificial Sequence
<220> FEATURE:
<223> OTHER INFORMATION: Primer

<400> SEQUENCE: 7
tgtaaaacga cggccagttg taatgcccgc aacagtgc                      38

<210> SEQ ID NO 8
<211> LENGTH: 46
<212> TYPE: DNA
<213> ORGANISM: Artificial Sequence
<220> FEATURE:
<223> OTHER INFORMATION: Primer

<400> SEQUENCE: 8
caggaaacag ctatgaccta ggaggggta aggacactga ggatca              46

<210> SEQ ID NO 9
<211> LENGTH: 42
<212> TYPE: DNA
<213> ORGANISM: Artificial Sequence
<220> FEATURE:
<223> OTHER INFORMATION: Primer

<400> SEQUENCE: 9
tgtaaaacga cggccagtca ataccaatgt tggcccCttt tg                 42

<210> SEQ ID NO 10
<211> LENGTH: 44
<212> TYPE: DNA
<213> ORGANISM: Artificial Sequence
<220> FEATURE:
<223> OTHER INFORMATION: Primer

<400> SEQUENCE: 10
caggaaacag ctatgaccca ccctgtctca aaaatacaca aagg               44

<210> SEQ ID NO 11
<211> LENGTH: 40
<212> TYPE: DNA
<213> ORGANISM: Artificial Sequence
<220> FEATURE:
<223> OTHER INFORMATION: Primer

<400> SEQUENCE: 11
tgtaaaacga cggccagtag caaaaactct gcaaaggggc           40

<210> SEQ ID NO 12
<211> LENGTH: 37
<212> TYPE: DNA
<213> ORGANISM: Artificial Sequence
<220> FEATURE:
<223> OTHER INFORMATION: Primer

<400> SEQUENCE: 12
caggaaacag ctatgaccac caaggtgggg actgccg              37

<210> SEQ ID NO 13
<211> LENGTH: 35
<212> TYPE: DNA
<213> ORGANISM: Artificial Sequence
<220> FEATURE:
<223> OTHER INFORMATION: Primer

<400> SEQUENCE: 13
tgtaaaacga cggccagtac acctacccca agtct                35

<210> SEQ ID NO 14
<211> LENGTH: 39
<212> TYPE: DNA
<213> ORGANISM: Artificial Sequence
<220> FEATURE:
<223> OTHER INFORMATION: Primer

<400> SEQUENCE: 14
caggaaacag ctatgacctg ggatgtcatc tctacagca            39

<210> SEQ ID NO 15
<211> LENGTH: 39
<212> TYPE: DNA
<213> ORGANISM: Artificial Sequence
<220> FEATURE:
<223> OTHER INFORMATION: Primer

<400> SEQUENCE: 15
tgtaaaacga cggccagtcg agcagggttc agatcccag            39

<210> SEQ ID NO 16
<211> LENGTH: 40
<212> TYPE: DNA
<213> ORGANISM: Artificial Sequence
<220> FEATURE:
<223> OTHER INFORMATION: Primer

<400> SEQUENCE: 16
caggaaacag ctatgaccga atccgggctt gctgtgggag           40

<210> SEQ ID NO 17
<211> LENGTH: 40
<212> TYPE: DNA
<213> ORGANISM: Artificial Sequence
<220> FEATURE:
<223> OTHER INFORMATION: Primer

<400> SEQUENCE: 17
tgtaaaacga cggccagtgt tttgctccac tgaggagccc           40

<210> SEQ ID NO 18

```
<211> LENGTH: 36
<212> TYPE: DNA
<213> ORGANISM: Artificial Sequence
<220> FEATURE:
<223> OTHER INFORMATION: Primer

<400> SEQUENCE: 18
caggaaacag ctatgacctg aaattcgtgg cctatt                    36
```

SULFOTRANSFERASE 1A3 SEQUENCE VARIANTS

CROSS-REFERENCE TO RELATED APPLICATIONS

This application is a continuation of U.S. Ser. No. 10/348,546, filed Jan. 21, 2003, which has matured into U.S. Pat. No. 7,425,624 on Sep. 16, 2008.

STATEMENT AS TO FEDERALLY SPONSORED RESEARCH

This invention was made with government support under grant no. GM61388 awarded by the National Institutes of Health. The government has certain rights in the invention.

TECHNICAL FIELD

This invention relates to sulfotransferase 1A3 nucleic acid and amino acid sequence variants.

BACKGROUND OF THE INVENTION

Sulfate conjugation is an important pathway in the biotransformation of many neurotransmitters, hormones, drugs and other xenobiotics, and is catalyzed by cytosolic sulfotransferase enzymes designated "SULT." SULT enzymes are encoded by a gene superfamily that, in mammals, is divided into two families: SULT1 or phenol SULTs, and SULT2 or hydroxysteroid SULTs. The SULT1 and SULT2 families share at least 45% amino acid sequence identity, while members of subfamilies within each family share at least 60% amino acid sequence identity. SULT1 subfamilies include the phenol (1A), thyroid hormone (1B), hydroxyarylamine (1C), and estrogen (1E) SULTs. SULT2 subfamilies include two hydroxysteroid SULTs, 2A1 and 2B1.

Members of the SULT1A subfamily, including SULT1A3, catalyze the sulfate conjugation of substrates such as dopamine, serotonin and other catchol monoamines, and Troglitazone. SULT1A3 is expressed in liver, brain, jejunum, kidney, and blood platelets. SULT1A3 also is referred to as "STM," "M-PST," or "TL-PST."

SUMMARY OF THE INVENTION

The invention is based on the discovery of sequence variants that occur in both coding and non-coding regions of SULT1A3 nucleic acids. Certain SULT1A3 nucleotide sequence variants encode SULT1A3 enzymes that are associated with individual differences in enzymatic activity. Other SULT1A3 nucleotide sequence variants in non-coding regions of the SULT1A3 nucleic acid may alter regulation of transcription and/or splicing of the SULT1A3 nucleic acid. Discovery of these sequence variants allows individual differences in the sulfate conjugation of dopamine and similar molecules in humans to be assessed such that particular treatment regimens can be tailored to an individual based on the presence or absence of one or more sequence variants. Identification of SULT1A3 nucleotide sequence variants also allows assessment of an individual's predisposition to conditions such as schizophrenia, affective disorders, and renal disease.

The invention features an isolated nucleic acid molecule containing a SULT1A3 nucleic acid sequence, wherein the nucleic acid molecule is at least ten nucleotides in length, and wherein the SULT1A3 nucleic acid sequence contains a nucleotide sequence variant relative to SEQ ID NO:1. The nucleotide sequence variant can be at a position selected from the group consisting of: a) position 702 relative to the adenine of the SULT1A3 translation initiation codon; b) position 96 relative to the guanine in the splice donor site of intron 1C; c) position 1325 relative to the guanine in the splice donor site of intron 1A; and d) position 1369 relative to the guanine in the splice donor site of intron 4. The nucleotide sequence variant can be a nucleotide substitution. The nucleotide sequence variant can be a thymine substitution for guanine at position 702 relative to the adenine of the SULT1A3 translation initiation codon. The nucleotide sequence variant at position 96 relative to the guanine in the splice donor site of intron 1C can be a thymine substitution for cytosine. The nucleotide sequence variant at position 1325 relative to the guanine in the splice donor site of intron 1A can be a guanine substitution for adenine. The nucleotide sequence variant at position 1369 relative to the guanine in the splice donor site of intron 4 can be an adenine substitution for guanine.

In another aspect, the invention features an isolated nucleic acid encoding a SULT1A3 polypeptide, wherein the polypeptide contains a SULT1A3 amino acid sequence variant relative to the amino acid sequence of SEQ ID NO:4, wherein the amino acid sequence variant is at residue 234.

The invention also features an isolated SULT1A3 polypeptide, wherein the polypeptide contains a SULT1A3 amino acid sequence variant relative to the amino acid sequence of SEQ ID NO:4, wherein the amino acid sequence variant is at residue 234. The amino acid sequence variant at residue 234 can be asparagine.

In another aspect, the invention features an article of manufacture containing a substrate, wherein the substrate contains a population of isolated SULT1A3 nucleic acid molecules of claim 1. The substrate can have a plurality of discrete regions, wherein each region contains a different population of isolated SULT1A3 nucleic acid molecules. Each population of molecules can contain a different SULT1A3 nucleotide sequence variant.

In yet another aspect, the invention features a method for determining if a mammal is predisposed to schizophrenia. The method can include: a) obtaining a biological sample from the mammal, and b) detecting the presence or absence of a SULT1A3 nucleotide sequence variant in the sample, wherein predisposition to the schizophrenia is determined based on the presence or absence of the variant. The method can further include detecting the presence or absence of a plurality of the SULT1A3 nucleotide sequence variants in the sample to obtain a variant profile of the mammal, wherein predisposition to the schizophrenia is determined based on the variant profile.

The invention also features a method for assisting a medical or research professional. The method can include: a) obtaining a biological sample from a mammal, and b) detecting the presence or absence of a plurality of SULT1A3 nucleotide sequence variants in the sample to obtain a variant profile of the mammal. The method can further include communicating the profile to the medical or research professional.

In another aspect, the invention features an isolated nucleic acid molecule containing a SULT1A3 nucleic acid sequence, wherein the nucleic acid molecule is at least ten nucleotides in length, and wherein the SULT1A3 nucleic acid sequence has at least 99% sequence identity to a region of SEQ ID NO:3. Nucleotide 702 relative to the adenine of the SULT1A3 translation initiation codon can be a thymine, and the region can include nucleotides 650 to 750 of SEQ ID NO:3 relative to the adenine of the SULT1A3 translation initiation codon.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 1 is the nucleotide sequence of the reference SULT1A3 (SEQ ID NO:1) and its complement (SEQ ID NO:2). Exons are depicted in bold type. Single nucleotide polymorphisms (SNPs) are italicized and in bold type. Primers are underlined. Translation start and stop codons are double-underlined.

FIG. 2A is an mRNA sequence (SEQ ID NO:3) containing the cDNA sequence of the reference SULT1A3 (nucleotides 139 to 885). FIG. 2B is the amino acid sequence (SEQ ID NO:4) of the reference SULT1A3.

FIG. 3 is a schematic of the location of polymorphisms within the SULT1A3 amino acid sequence in Caucasian Americans (CA) and African Americans (AA).

DETAILED DESCRIPTION

The invention features SULT1A3 nucleotide and SULT1A3 amino acid sequence variants. SULT1A3 catalyzes the transfer of inorganic sulfate to molecules such as dopamine, serotonin and other catechol monoamines, and Troglitazone, and uses 3'-phosphoadenosine-5'-phosphosulfate (PAPS) as the sulfate donor. Sulfation typically detoxifies compounds, as the resulting ionized, organic sulfates are more readily excreted than the unsulfated compounds. Furthermore, functional groups that may interact with biological macromolecules such as nucleic acids or proteins can be masked by the sulfate moiety. Genetically based variations in SULT1A3 activity may affect the metabolism of molecules such as dopamine. For example, a subject with decreased SULT1A3 activity may have higher circulating levels of dopamine, which could lead to schizophrenia or related disorders. Thus, detecting sulfotransferase nucleic acid and amino acid sequence variants can facilitate prediction of therapeutic efficacy and toxicity of drugs on an individual basis, as well as prediction of an individual's ability to biotransform molecules such as dopamine.

Nucleic Acid Molecules

The invention features isolated nucleic acids that include a SULT1A3 nucleic acid sequence. The SULT1A3 nucleic acid sequence includes a nucleotide sequence variant and nucleotides flanking the sequence variant. As used herein, "isolated nucleic acid" refers to a nucleic acid that is separated from other nucleic acid molecules that are present in a mammalian genome, including nucleic acids that normally flank one or both sides of the nucleic acid in a mammalian genome (e.g., nucleic acids that encode non-SULT1A3 proteins). The term "isolated" as used herein with respect to nucleic acids also includes any non-naturally-occurring nucleic acid sequence, since non-naturally-occurring sequences are not found in nature and do not have immediately contiguous sequences in a naturally-occurring genome.

An isolated nucleic acid can be, for example, a DNA molecule, provided one or both of the nucleic acid sequences normally found immediately flanking that DNA molecule in a naturally-occurring genome (one at the 5' end and one at the 3' end) is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as recombinant DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Nucleic acids of the invention are at least about 8 nucleotides in length. For example, a nucleic acid can be about 8, 9, 10-20 (e.g., 11, 12, 13, 14, 15, 16, 17, 18, 19, or 20 nucleotides in length), 20-50, 50-100 or greater than 100 nucleotides in length (e.g., greater than 150, 200, 250, 300, 350, 400, 450, 500, 750, or 1000 nucleotides in length). Nucleic acids of the invention can be in a sense or an antisense orientation, can be complementary to the SULT1A3 reference sequence, and can be DNA, RNA, or nucleic acid analogs. Nucleic acid analogs can be modified at the base moiety, sugar moiety, or phosphate backbone to improve, for example, stability, hybridization, or solubility of a nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered, morpholino ring, or peptide nucleic acids, in which the deoxyphosphate backbone is replaced by a pseudopeptide backbone and the four bases are retained. See, for example, Summerton and Weller (1997) *Antisense Nucleic Acid Drug Dev.* 7:187-195; and Hyrup et al. (1996) *Bioorgan. Med. Chem.* 4:5-23. In addition, the deoxyphosphate backbone can be replaced with, for example, a phosphorothioate or phosphorodithioate backbone, a phosphoroamidite, or an alkyl phosphotriester backbone.

As used herein, "nucleotide sequence variant" refers to any alteration in the SULT1A3 reference sequence, and includes variations that occur in coding and non-coding regions, including exons, introns, and untranslated sequences. Nucleotides are referred to herein by the standard one-letter designation (A, C, G, or T). Variants include single nucleotide substitutions, deletions of one or more nucleotides, and insertions of one or more nucleotides. The reference SULT1A3 genomic nucleic acid sequence is provided in FIG. 1 (SEQ ID NO:1 and SEQ ID NO:2) and in GenBank (Accession No. U20499). The reference SULT1A3 mRNA including the SULT1A3 cDNA is provided in FIG. 2A (SEQ ID NO:3) and the corresponding amino acid sequence is provided in FIG. 2B (SEQ ID NO:4). Both the mRNA and the amino acid sequences also can be found in GenBank (Accession No. L19956). Transcripts of the SULT1A3 gene are subject to alternative splicing, but this does not result in multiple mRNAs since the alternative splicing takes place in the 5' untranslated region and affects only exons 1C, 1B, and 1A. The SULT1A3 cDNA is encoded by exons 2-7 and the 5' end of exon 8.

The nucleic acid and amino acid reference sequences also are referred to herein as "wild type" (WT). As used herein, "untranslated sequence" includes 5' and 3' flanking regions that are outside of the mRNA as well as 5' and 3' untranslated regions (5'-UTR or 3'-UTR) that are part of the mRNA, but are not translated. Positions of nucleotide sequence variants in 5' untranslated sequences are designated as "−X" relative to the "A" in the initiation codon; positions of nucleotide sequence variants in the coding sequence and 3' untranslated sequence are designated as "+X" or "X" relative to the "A" in the initiation codon. Nucleotide sequence variants that occur in introns are designated as "+X" or "X" relative to "G" in the splice donor site (GT) or as "−X" relative to the "G" in the splice acceptor site (AG).

In some embodiments, a SULT1A3 nucleotide sequence variant encodes a SULT1A3 polypeptide containing a SULT1A3 amino acid sequence variant. The term "polypeptide" refers to a chain of at least four amino acid residues (e.g., 4-8, 9-12, 13-15, 16-18, 19-21, 22-100, 100-150, 150-200, 200-300 residues, or a full-length SULT1A3 polypeptide). SULT1A3 polypeptides may or may not have sulfotransferase catalytic activity, or may have activity that is altered relative to the reference SULT1A3 polypeptide. Polypeptides that do not have activity or that have altered activity can be useful for diagnostic purposes (e.g., for producing antibodies having specific binding affinity for variant sulfotransferase polypeptides).

Corresponding SULT1A3 polypeptides, irrespective of length, that differ in amino acid sequence are herein referred to as allozymes. For example, a SULT1A3 nucleic acid sequence that includes a thymine at nucleotide 702 encodes a SULT1A3 polypeptide having an asparagine at amino acid residue 234. This polypeptide (Lys234Asn) would be considered an allozyme with respect to the reference SULT1A3 polypeptide that contains a lysine at amino acid residue 234.

SULT1A3 allozymes as described above are encoded by a series of sulfotransferase alleles. These alleles represent SULT1A3 nucleic acid sequences containing nucleotide sequence variants, typically multiple nucleotide sequence variants, within coding and non-coding sequences. Representative examples of single nucleotide sequence variants are disclosed in Table 2. Alleles encoding Lys234Asn are commonly observed in African Americans (allele frequencies≧1%). The relatively large number of alleles and allozymes for SULT1A3 indicates the potential complexity of SULT pharmacogenetics. Such complexity emphasizes the need for determining single nucleotide sequence variants, (i.e., single nucleotide polymorphisms, SNPs) as well as complete haplotypes (i.e., the set of alleles on one chromosome or a part of a chromosome) of patients.

Certain SULT1A3 nucleotide sequence variants do not alter the amino acid sequence. Such variants, however, could alter regulation of transcription as well as mRNA stability. SULT1A3 nucleotide sequence variants can occur in intron sequences, for example, within introns 1A, 1B, 1C, 2, 3, 4, 5, 6, or 7. In particular, the nucleotide sequence variant can include a thymine at nucleotide 96 of intron 1C, a cytosine at nucleotide 99 of intron 1C, or a thymine at nucleotide 105 of intron 1C. The nucleotide sequence variant can include a guanine at nucleotide 1325 of intron 1A. Intron 4 variants can include an adenine at nucleotide 1369, and intron 7 variants can include a thymine at nucleotide 113.

SULT1A3 nucleotide sequence variants that do not change the amino acid sequence also can be within an exon or in 5' or 3' untranslated sequences. For example, a SULT1A3 variant can include a guanine at nucleotide 105 relative to the adenine in the translation initiation site, or an adenine at nucleotide 843 relative to the adenine in the translation initiation site.

In some embodiments, nucleic acid molecules of the invention can have at least 98% (e.g., 98.5%, 99.0%, 99.5%, 99.6%, 99.7%, 99.8%, 99.9%, or 100%) sequence identity with a region of SEQ ID NO:1 or SEQ ID NO:3 that includes one or more variants described herein. The region of SEQ ID NO:1 or SEQ ID NO:3 is at least 15 nucleotides in length (e.g., 50, 60, 70, 75, 100, 150 or more nucleotides in length). For example, a nucleic acid molecule can have at least 99% identity with a region of SEQ ID NO:1 containing nucleotides −150 to 1000, −250 to −155, −150 to −75, −75 to −30, −25 to 50, 55 to 150, 115 to 200, 205 to 275, 300 to 375, 375 to 475, 455 to 525, 530 to 630, 650 to 750, 755 to 850, 800 to 900, 855 to 950, 955 to 1050, 1005 to 1100, or 1050 to 1150 relative to the adenine of the SULT1A3 translation initiation codon, nucleotides 50 to 150 of SEQ ID NO:1 relative to the guanine in the splice donor site of SULT1A3 intron 1C, nucleotides 1275 to 1375 of SEQ ID NO:1 relative to the guanine in the splice donor site of SULT1A3 intron 1A, nucleotides 1300 to 1400 of SEQ ID NO:1 relative to the guanine in the splice donor site of intron 4, or nucleotides 75 to 160 of SEQ ID NO:1 relative to the guanine in the splice donor site of SULT1A3 intron 7, where the nucleotide sequence of SEQ ID NO:1 includes one or more (e.g., one, two, three, four, five, or more than five) of the variants described herein. For example, the nucleotide sequence of SEQ ID NO:1 can have a guanine at nucleotide 105 relative to the adenine of the SULT1A3 translation initiation codon, a thymine at nucleotide 702 relative to the adenine of the SULT1A3 translation initiation codon, an adenine at nucleotide 843 relative to the adenine of the SULT1A3 translation initiation codon, a thymine at nucleotide 96 relative to the guanine in the splice donor site of intron 1C, a cytosine at nucleotide 99 relative to the guanine in the splice donor site of intron 1C, a thymine at nucleotide 105 relative to the guanine in the splice donor site of intron 1C, a guanine at nucleotide 1325 relative to the guanine in the splice donor site of intron 1A, an adenine at nucleotide 1369 relative to the guanine in the splice donor site of intron 4, or a thymine at nucleotide 113 relative to the guanine in the splice donor site of intron 7, and combinations thereof. The nucleotide sequence of SEQ ID NO:1 also can have an insertion of the sequence 5' CAGT 3' between nucleotides 83 and 84 relative to the guanine in the splice donor site of intron 3, an adenine at nucleotide 69 relative to the guanine in the splice donor site of intron 4, or an adenine at nucleotide 69 relative to the guanine in the splice donor site of intron 6. Alternatively, a nucleic acid molecule can have at least 99% identity with a region of SEQ ID NO:1 containing nucleotides 650 to 750, where the nucleotide sequence of SEQ ID NO:3 includes one or more (e.g., one, two, three, four, five, or more than five) of the variants described herein. For example, the nucleotide sequence of SEQ ID NO:3 can have a thymine at nucleotide 702 relative to the adenine of the SULT1A3 translation initiation codon. In some embodiments, the nucleotide sequence can contain at least two (e.g., two, three, four, five, or more than five) of the variants described herein.

Percent sequence identity is calculated by determining the number of matched positions in aligned nucleic acid sequences, dividing the number of matched positions by the total number of aligned nucleotides, and multiplying by 100. A matched position refers to a position in which identical nucleotides occur at the same position in aligned nucleic acid sequences. Percent sequence identity also can be determined for any amino acid sequence. To determine percent sequence identity, a target nucleic acid or amino acid sequence is compared to the identified nucleic acid or amino acid sequence using the BLAST 2 Sequences (Bl2seq) program from the stand-alone version of BLASTZ containing BLASTN version 2.0.14 and BLASTP version 2.0.14. This stand-alone version of BLASTZ can be obtained from Fish & Richardson's web site (fr.com/blast) or the U.S. government's National Center for Biotechnology Information web site (ncbi.nlm.nih.gov). Instructions explaining how to use the Bl2seq program can be found in the readme file accompanying BLASTZ.

Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C: \seq1.txt); -j is set to a file containing the second nucleic acid sequence to be compared (e.g., C: \seq2.txt); -p is set to blastn; -o is set to any desired file name (e.g., C:\output.txt); -q is set to −1; -r is set to 2; and all other options are left at their default setting. The following command will generate an output file containing a comparison between two sequences: C:\Bl2seq c:\seq1.txt -j c:\seq2.txt -p blastn -o c:\output.txt -q -1 -r 2. If the target sequence shares homology with any portion of the identified sequence, then the designated output file will present those regions of homology as aligned sequences. If the target sequence does not share homology with any portion of the identified sequence, then the designated output file will not present aligned sequences.

Once aligned, a length is determined by counting the number of consecutive nucleotides from the target sequence presented in alignment with sequence from the identified sequence starting with any matched position and ending with any other matched position. A matched position is any position where an identical nucleotide is presented in both the target and identified sequence. Gaps presented in the target sequence are not counted since gaps are not nucleotides. Likewise, gaps presented in the identified sequence are not counted since target sequence nucleotides are counted, not nucleotides from the identified sequence.

The percent identity over a particular length is determined by counting the number of matched positions over that length and dividing that number by the length followed by multiplying the resulting value by 100. For example, if (1) a 1000 nucleotide target sequence is compared to the sequence set forth in SEQ ID NO:3, (2) the Bl2seq program presents 850 nucleotides from the target sequence aligned with a region of the sequence set forth in SEQ ID NO:3 where the first and last nucleotides of that 850 nucleotide region are matches, and (3) the number of matches over those 850 aligned nucleotides is 750, then the 1000 nucleotide target sequence contains a length of 850 and a percent identity over that length of 88 (i.e., 750÷850×100=88).

It will be appreciated that different regions within a single nucleic acid target sequence that aligns with an identified sequence can each have their own percent identity. It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

Isolated nucleic acid molecules of the invention can be produced by standard techniques, including, without limitation, common molecular cloning and chemical nucleic acid synthesis techniques. For example, polymerase chain reaction (PCR) techniques can be used to obtain an isolated nucleic acid containing a SULT1A3 nucleotide sequence variant. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize a complementary DNA (cDNA) strand. Ligase chain reaction, strand displacement amplification, self-sustained sequence replication or nucleic acid sequence-based amplification also can be used to obtain isolated nucleic acids. See, for example, Lewis *Genetic Engineering News* 12(9):1 (1992); Guatelli et al. (1990) *Proc. Natl. Acad. Sci. USA*, 87:1874-1878; and Weiss (1991) Science 254:1292.

Isolated nucleic acids of the invention also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Isolated nucleic acids of the invention also can be obtained by mutagenesis. For example, the reference sequence depicted in FIG. 1 or 2A can be mutated using standard techniques such as, for example, oligonucleotide-directed mutagenesis and/or site-directed mutagenesis through PCR. See, *Short Protocols in Molecular Biology*, Chapter 8, Green Publishing Associates and John Wiley & Sons, Edited by Ausubel et al., 1992. Examples of positions that can be modified include those described above.

Vectors and Host Cells

The invention also provides vectors containing nucleic acids such as those described above. As used herein, a "vector" is a replicon, such as a plasmid, phage, or cosmid, into which another DNA segment may be inserted so as to bring about the replication of the inserted segment. The vectors of the invention can be expression vectors. An "expression vector" is a vector that includes one or more expression control sequences, and an "expression control sequence" is a DNA sequence that controls and regulates the transcription and/or translation of another DNA sequence.

In the expression vectors of the invention, the nucleic acid is operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

An expression vector can include a tag sequence designed to facilitate subsequent manipulation of the expressed nucleic acid sequence (e.g., purification or localization). Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide including at either the carboxyl or amino terminus.

The invention also provides host cells containing vectors of the invention. The term "host cell" is intended to include prokaryotic and eukaryotic cells into which a recombinant expression vector can be introduced. As used herein, "transformed" and "transfected" encompass the introduction of a nucleic acid molecule (e.g., a vector) into a cell by one of a number of techniques. Although not limited to a particular technique, a number of these techniques are well established within the art. Prokaryotic cells can be transformed with nucleic acids by, for example, electroporation or calcium chloride mediated transformation. Nucleic acids can be transfected into mammalian cells by techniques including, for example, calcium phosphate co-precipitation, DEAE-dextran-mediated transfection, lipofection, electroporation, or microinjection. Suitable methods for transforming and transfecting host cells are found in Sambrook et al., *Molecular Cloning: A Laboratory Manual* (2$^{nd}$ edition), Cold Spring Harbor Laboratory, New York (1989), and reagents for transformation and/or transfection are commercially available (e.g., Lipofectin (Invitrogen/Life Technologies); Fugene (Roche, Indianapolis, Ind.); and SuperFect (Qiagen, Valencia, Calif.)).

SULT1A3 Polypeptides

Isolated SULT1A3 polypeptides of the invention include an amino acid sequence variant relative to the reference SULT1A3 polypeptide (FIG. 2B, GenBank Accession No. L19956). The term "isolated" with respect to a SULT1A3 polypeptide refers to a polypeptide that has been separated from cellular components by which it is naturally accompanied. Typically, a SULT1A3 polypeptide is isolated when it is at least 60% (e.g., 65%, 70%, 75%, 80%, 90%, 95%, or 99%), by weight, free from proteins and naturally occurring organic molecules with which it is naturally associated. In general, an isolated polypeptide will yield a single major band on a non-reducing polyacrylamide gel.

SULT1A3 polypeptides of the invention include variants at residue 234. In particular, an asparagine residue can be substituted at position 234.

In some embodiments, the activity of a SULT1A3 polypeptide is altered relative to a SULT1A3 polypeptide having the reference amino acid sequence set forth in SEQ ID NO:4. Certain SULT1A3 allozymes can have reduced activity (e.g., Lys234Asn), while other allozymes can have activity that is comparable to the reference SULT1A3 polypeptide. Other allozymes can have increased activity relative to the reference SULT1A3 polypeptide. Activity of SULT1A3 polypeptides can be assessed in vitro using a sulfate acceptor substrate such as dopamine and a donor sulfate molecule such as PAPS. In general, recombinant SULT1A3 polypeptides can be incubated at 37° C. for approximately 60 minutes with 14 µM $^{35}$S-PAPS and 40 µM dopamine in a 3-[N-tris-(hydroxymethyl)methylamino]propanesulfonic acid (Taps) buffer (50 mM, pH 8.25). Reactions can be stopped by heating at 100° C. for 3 minutes. After centrifugation of the heated reaction, radioactivity in the supernatant can be assessed. SULT1A3 activity is expressed as nmoles of sulfate conjugated product formed per hour of incubation.

Other biochemical properties of allozymes, such as apparent $K_m$ values, also can be altered relative to the reference SULT1A3 polypeptide. Apparent $K_m$ values can be calculated, for example, by using the method of Wilkinson with a computer program written by Cleland. Wilkinson (1961) *Biochem. J.* 80:324-332; and Cleland (1963) *Nature* 198:463-365. The apparent $K_m$ values for dopamine can vary between different allozymes.

Isolated polypeptides of the invention can be obtained by, for example, extraction from a natural source (e.g., liver tissue), chemical synthesis, or by recombinant production in a host cell. To recombinantly produce SULT1A3 polypeptides, a nucleic acid sequence containing a SULT1A3 nucleotide sequence variant can be ligated into an expression vector that can be used to transform a bacterial or eukaryotic host cell (e.g., insect, yeast, or mammalian cells). In general, nucleic acid constructs include a regulatory sequence operably linked to a SULT1A3 nucleic acid sequence. Regulatory sequences do not typically encode a gene product, but instead affect the expression of the nucleic acid sequence. In bacterial systems, a strain of *Escherichia coli* such as BL-21 can be used. Suitable *E. coli* vectors include the pGEX series of vectors (Amersham Biosciences Corp., Piscataway, N.J.) that produce fusion polypeptides with glutathione S-transferase (GST). Transformed *E. coli* typically are grown exponentially and then stimulated with isopropylthiogalactopyranoside (IPTG) to induce expression of the fusion polypeptide. In general, such fusion polypeptides are soluble and can be purified easily from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In eukaryotic host cells, a number of viral-based expression systems can be utilized to express SULT1A3 variant polypeptides. A nucleic acid encoding a polypeptide of the invention can be cloned into, for example, a baculoviral vector such as pBlueBac (Invitrogen, Carlsbad, Calif.) and then used to co-transfect insect cells such as *Spodoptera frugiperda* (Sf9) cells with wild type DNA from *Autographa*

*californica* multiply enveloped nuclear polyhedrosis virus (AcMNPV). Recombinant viruses producing polypeptides of the invention can be identified by standard methodology. Alternatively, a nucleic acid encoding a polypeptide of the invention can be introduced into a SV40, retroviral, or vaccinia based viral vector and used to infect suitable host cells.

Mammalian cell lines that stably express SULT1A3 variant polypeptides can be produced using expression vectors with the appropriate control elements and a selectable marker. For example, the eukaryotic expression vectors pCR3.1 (Invitrogen) and p91023(B) (see Wong et al. (1985) *Science* 228:810-815) are suitable for expression of sulfotransferase variant polypeptides in, for example, Chinese hamster ovary (CHO) cells, COS-1 cells, human embryonic kidney 293 cells, NIH3T3 cells, BHK21 cells, MDCK cells, and human vascular endothelial cells (HUVEC). Following introduction of the expression vector by electroporation, lipofection, calcium phosphate or calcium chloride co-precipitation, DEAE dextran, or other suitable transfection method, stable cell lines can be selected, e.g., by antibiotic resistance to G418, kanamycin, or hygromycin. Alternatively, amplified sequences can be ligated into a mammalian expression vector such as pcDNA3 (Invitrogen) and then transcribed and translated in vitro using wheat germ extract or rabbit reticulocyte lysate.

SULT1A3 variant polypeptides can be purified by known chromatographic methods including DEAE ion exchange, gel filtration, and hydroxylapatite chromatography. See, e.g., Van Loon and Weinshilboum (1990) *Drug Metab. Dispos.* 18:632-638; and Van Loon et al. (1992) *Biochem. Pharmacol.* 44:775-785. SULT1A3 polypeptides can be "engineered" to contain an amino acid sequence that allows the polypeptide to be captured onto an affinity matrix. For example, a tag such as c-myc, hemagglutinin, polyhistidine, or Flag™ (Kodak) can be used to aid polypeptide purification. Such tags can be inserted anywhere within the polypeptide including at either the carboxyl or amino terminus. Other fusions that can be useful include enzymes that aid in the detection of the polypeptide, such as alkaline phosphatase. Immunoaffinity chromatography also can be used to purify SULT1A3 polypeptides.

Non-Human Mammals

The invention features non-human mammals that include SULT1A3 nucleic acids of the invention, as well as progeny and cells of such non-human mammals. Non-human mammals include, for example, rodents such as rats, guinea pigs, and mice, and farm animals such as pigs, sheep, goats, horses, and cattle. Non-human mammals of the invention can express a SULT1A3 nucleotide sequence variant in addition to an endogenous SULT1A3 nucleic acid (e.g., a transgenic non-human mammal that includes a SULT1A3 nucleic acid molecule randomly integrated into its genome). Alternatively, an endogenous SULT1A3 nucleic acid can be replaced by a SULT1A3 nucleic acid molecule containing a SULT1A3 nucleotide sequence variant through homologous recombination. See, Shastry (1998) *Mol. Cell. Biochem.* 181:163-179, for a review of gene targeting technology.

In one embodiment, non-human mammals are produced that lack an endogenous SULT1A3 nucleic acid (i.e., a knockout), and then a SULT1A3 variant nucleic acid of the invention is introduced into the knockout non-human mammal. Nucleic acid constructs used for producing knockout non-human mammals can include a nucleic acid sequence encoding a selectable marker, which generally is used to interrupt the targeted exon site by homologous recombination. Typically, the selectable marker is flanked by sequences homologous to the sequences flanking the desired insertion site. It is not necessary for the flanking sequences to be immediately adjacent to the desired insertion site. Suitable markers for positive drug selection include, for example, the aminoglycoside 3N phosphotransferase gene that imparts resistance to geneticin (G418, an aminoglycoside antibiotic), and other antibiotic resistance markers, such as the hygromycin-B-phosphotransferase gene that imparts hygromycin resistance. Other selection systems can include negative-selection markers such as the thymidine kinase (TK) gene from herpes simplex virus. Constructs utilizing both positive and negative drug selection also can be used. For example, a construct can contain the aminoglycoside phosphotransferase gene and the TK gene. In this system, cells are selected that are resistant to G418 and sensitive to gancyclovir.

To create non-human mammals having a particular gene inactivated in all cells, it is necessary to introduce a knockout construct into the germ cells (sperm or eggs, i.e., the "germ line") of the desired species. Genes or other DNA sequences can be introduced into the pronuclei of fertilized eggs by microinjection. Following pronuclear fusion, the developing embryo may carry the introduced gene in all its somatic and germ cells since the zygote is the mitotic progenitor of all cells in the embryo. Since targeted insertion of a knockout construct is a relatively rare event, it typically is desirable to generate and screen a large number of animals when employing such an approach. Because of this, it can be advantageous to work with the large cell populations and selection criteria that are characteristic of cultured cell systems. However, for production of knockout animals from an initial population of cultured cells, it is necessary that a cultured cell containing the desired knockout construct be capable of generating a whole animal. This generally is accomplished by placing the cell into a developing embryo environment of some sort.

Cells capable of giving rise to at least several differentiated cell types are "pluripotent." Pluripotent cells capable of giving rise to all cell types of an embryo, including germ cells, are hereinafter termed "totipotent" cells. Totipotent murine cell lines (embryonic stem, or "ES" cells) have been isolated by culture of cells derived from very young embryos (blastocysts). Such cells are capable, upon incorporation into an embryo, of differentiating into all cell types, including germ cells, and can be employed to generate animals lacking an endogenous SULT1A3 nucleic acid. That is, cultured ES cells can be transformed with a knockout construct and cells selected in which the SULT1A3 gene is inactivated.

Nucleic acid constructs can be introduced into ES cells, for example, by electroporation or other standard technique. Selected cells can be screened for gene targeting events. For example, the polymerase chain reaction (PCR) can be used to confirm the presence of the transgene.

The ES cells further can be characterized to determine the number of targeting events. For example, genomic DNA can be harvested from ES cells and used for Southern analysis. See, for example, Sections 9.37-9.52 of Sambrook et al., *Molecular Cloning, A Laboratory Manual*, second edition, Cold Spring Harbor Press, Plainview; NY, 1989.

To generate a knockout animal, ES cells having at least one inactivated SULT1A3 allele can be incorporated into a developing embryo. This can be accomplished through injection into the blastocyst cavity of a murine blastocyst-stage embryo, by injection into a morula-stage embryo, by co-culture of ES cells with a morula-stage embryo, or through fusion of the ES cell with an enucleated zygote. The resulting embryo is raised to sexual maturity and bred in order to obtain animals whose cells (including germ cells) carry the inactivated SULT1A3 allele. If the original ES cell was heterozygous for the inactivated SULT1A3 allele, several of these animals can be bred with each other in order to generate animals homozygous for the inactivated allele.

Alternatively, direct microinjection of DNA into eggs can be used to avoid the manipulations required to generate an animal from a cultured cell. Fertilized eggs are "totipotent," i.e., capable of developing into an adult without further substantive manipulation other than implantation into a surrogate mother. To enhance the probability of homologous recombination when eggs are directly injected with knockout constructs, it is useful to incorporate at least about 8 kb of homologous DNA into the targeting construct. In addition, it is also useful to prepare the knockout constructs from isogenic DNA.

Embryos derived from microinjected eggs can be screened for homologous recombination events in several ways. For example, if the SULT1A3 gene is interrupted by a coding region that produces a detectable (e.g., fluorescent) gene product, then the injected eggs can be cultured to the blastocyst stage and analyzed for presence of the indicator polypeptide. Embryos with fluorescing cells, for example, are then implanted into a surrogate mother and allowed to develop to term. Alternatively, injected eggs are allowed to develop and DNA from the resulting pups analyzed by PCR or RT-PCR for evidence of homologous recombination.

Nuclear transplantation also can be used to generate non-human mammals of the invention. For example, fetal fibroblasts can be genetically modified such that they contain an inactivated endogenous SULT1A3 gene and express a SULT1A3 nucleic acid of the invention, and then fused with enucleated oocytes. After activation of the oocytes, the eggs are cultured to the blastocyst stage, and implanted into a recipient. See, Cibelli et al. (1998) *Science* 280:1256-1258. Adult somatic cells including, for example, cumulus cells and mammary cells, can be used to produce animals such as mice and sheep, respectively. See, for example, Wakayama et al. (1998) *Nature* 394:369-374; and Wilmut et al. (1997) *Nature* 385:810-813. Nuclei can be removed from genetically modified adult somatic cells and transplanted into enucleated oocytes. After activation, the eggs can be cultured to the 2-8 cell stage, or to the blastocyst stage, and implanted into a suitable recipient. Wakayama, T. et al., 1998, supra.

Non-human mammals of the invention such as mice can be used to screen, for example, toxicity of compounds that are substrates for SULT1A3 polypeptides, drugs that alter SULT1A3 polypeptide activity, or for carcinogenesis. For example, SULT1A3 polypeptide activity or toxicity can be assessed in a first group of such non-human mammals in the presence of a particular compound, and compared with SULT1A3 polypeptides activity or toxicity in a corresponding control group in the absence of the compound. As used herein, suitable compounds include biological macromolecules such as an oligonucleotide (RNA or DNA) or a polypeptide of any length, a chemical compound, a mixture of chemical compounds, or an extract isolated from bacterial, plant, fungal, or animal matter. The concentration of compound to be tested depends on the type of compound and in vitro test data.

Non-human mammals can be exposed to test compounds by any route of administration, including enterally and parenterally. For example, a test compound can be administered parenterally through inhalation, or by intranasal, intravascular, intramuscular, or subcutaneous administration. Enteral routes include sublingual and oral administration. Compounds can be prepared for parenteral administration in the form of liquid solutions or suspensions; for oral administration in the form of tablets or capsules; or for intranasal administration in the form of powders, nasal drops, or aerosols. Compounds can be prepared for other routes of administration using standard techniques. Test compounds can be mixed with non-toxic excipients or carriers before administration. Inhalation formulations can include aqueous solutions containing, for example, polyoxyethylene-9-lauryl ether, glycocholate, or deoxycholate. Other formulations may contain sterile water or saline, or polyalkylene glycols such as polyethylene glycol.

Detecting SULT1A3 Sequence Variants

The invention also provides methods for detecting SULT1A3 sequence variants. SULT1A3 nucleotide sequence variants can be detected, for example, by sequencing exons, introns, 5' untranslated sequences, or 3' untranslated sequences, by performing allele-specific hybridization, allele-specific restriction digests, mutation specific polymerase chain reactions (MSPCR), by single-stranded conformational polymorphism (SSCP) detection (Schafer et al. (1995) *Nat. Biotechnol.* 15:33-39), denaturing high performance liquid chromatography (DHPLC, Underhill et al. (1997) *Genome Res.* 7:996-1005), or infrared matrix-assisted laser desorption/ionization (IR-MALDI) mass spectrometry (WO 99/57318), and combinations of such methods.

Genomic DNA generally is used in the analysis of SULT1A3 nucleotide sequence variants. Genomic DNA typically is extracted from a biological sample such as a peripheral blood sample, but also can be extracted from other biological samples, including tissues (e.g., mucosal scrapings of the lining of the mouth or from renal or hepatic tissue). Standard methods can be used to extract genomic DNA from a blood or tissue sample, including, for example, phenol extraction. Alternatively, genomic DNA can be extracted with kits such as the QIAamp® Tissue Kit (Qiagen, Valencia, Calif.), Wizard® Genomic DNA purification kit (Promega, Madison, Wis.) and the A.S.A.P.™ Genomic DNA isolation kit (Boehringer Mannheim, Indianapolis, Ind.).

Typically, an amplification step is performed before proceeding with the detection method. For example, exons or introns of the SULT1A3 gene can be amplified and then directly sequenced. Dye primer sequencing can be used to increase the accuracy of detecting heterozygous samples.

Allele specific hybridization also can be used to detect SULT1A3 nucleotide sequence variants, including complete haplotypes of a mammal. See, Stoneking et al. (1991) *Am. J. Hum. Genet.* 48:370-382; and Prince et al. (2001) *Genome Res.* 11:152-162. In practice, samples of DNA or RNA from one or more mammals can be amplified using pairs of primers and the resulting amplification products can be immobilized on a substrate (e.g., in discrete regions). Hybridization conditions can be selected such that a nucleic acid probe can specifically bind to the sequence of interest, e.g., the SULT1A3 nucleic acid molecule containing a particular SULT1A3 nucleotide sequence variant. Such hybridizations typically are performed under high stringency, as some nucleotide sequence variants include only a single nucleotide difference. High stringency conditions can include, for example, the use of low ionic strength solutions and high temperatures for washing. For example, nucleic acid molecules can be hybridized at 42° C. in 2×SSC (0.3 M NaCl/0.03 M sodium citrate/0.1% sodium dodecyl sulfate (SDS) and washed in 0.1×SSC (0.015 M NaCl/0.0015 M sodium citrate), 0.1% SDS at 65° C. Hybridization conditions can be adjusted to account for unique features of the nucleic acid molecule, including length and sequence composition. Probes can be labeled (e.g., fluorescently) to facilitate detection. In some embodiments, one of the primers used in the amplification reaction is biotinylated (e.g., 5' end of reverse primer) and the resulting biotinylated amplification product is immobilized on an avidin or streptavidin coated substrate.

Allele-specific restriction digests can be performed in the following manner. For SULT1A3 nucleotide sequence variants that introduce a restriction site, restriction digest with the particular restriction enzyme can differentiate the alleles. For SULT1A3 nucleotide sequence variants that do not alter a common restriction site, mutagenic primers can be designed that introduce a restriction site when the variant allele is present or when the wild type allele is present. A portion of a SULT1A3 nucleic acid can be amplified using the mutagenic primer and a wild type primer, followed by digest with the appropriate restriction endonuclease.

Certain variants, such as insertions or deletions of one or more nucleotides, can change the size of the DNA fragment encompassing the variant. The insertion or deletion of nucleotides can be assessed by amplifying the region encompassing the variant and determining the size of the amplified products in comparison with size standards. For example, a region of a SULT1A3 nucleic acid can be amplified using a primer set from either side of the variant. One of the primers typically is labeled, for example, with a fluorescent moiety, to facilitate sizing. The amplified products can be electrophoresed through acrylamide gels with a set of size standards that are labeled with a fluorescent moiety that differs from the primer.

PCR conditions and primers can be developed that amplify a product only when the variant allele is present or only when the wild type allele is present (MSPCR or allele-specific PCR). For example, patient DNA and a control can be amplified separately using either a wild type primer or a primer specific for the variant allele. Each set of reactions is then examined for the presence of amplification products using standard methods to visualize the DNA. For example, the reactions can be electrophoresed through an agarose gel and the DNA visualized by staining with ethidium bromide or other DNA intercalating dye. In DNA samples from heterozygous patients, reaction products would be detected in each reaction. Patient samples containing solely the wild type allele would have amplification products only in the reaction using the wild type primer. Similarly, patient samples containing solely the variant allele would have amplification products only in the reaction using the variant primer. Allele-specific PCR also can be performed using allele-specific primers that introduce priming sites for two universal energy-transfer-labeled primers (e.g., one primer labeled with a green dye such as fluoroscein and one primer labeled with a red dye such as sulforhodamine). Amplification products can be analyzed for green and red fluorescence in a plate reader. See, Myakishev et al. (2001) *Genome* 11:163-169.

Mismatch cleavage methods also can be used to detect differing sequences by PCR amplification, followed by hybridization with the wild type sequence and cleavage at points of mismatch. Chemical reagents, such as carbodiimide or hydroxylamine and osmium tetroxide can be used to modify mismatched nucleotides to facilitate cleavage.

Alternatively, SULT1A3 allozymes can be detected by antibodies that have specific binding affinity for the particular allozymes. SULT1A3 allozymes can be produced in various ways, including recombinantly, as discussed above. Host animals such as rabbits, chickens, mice, guinea pigs and rats can be immunized by injection of a particular SULT1A3 allozyme. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin and dinitrophenol. Polyclonal antibodies are heterogenous populations of antibody molecules that are contained in the sera of the immunized animals. Monoclonal antibodies, which are homogeneous populations of antibodies to a particular antigen, can be prepared using a SULT1A3 allozyme and standard hybridoma technology. In particular, monoclonal antibodies can be obtained by any technique that provides for the production of antibody molecules by continuous cell lines in culture such as described by Kohler et al. (1975) *Nature* 256:495, the human B-cell hybridoma technique (Kosbor et al. (1983) *Immunology Today* 4:72; Cole et al. (1983) *Proc. Natl. Acad. Sci. USA* 80:2026), and the EBV-hybridoma technique (Cole et al., *Monoclonal Antibodies and Cancer Therapy*, Alan R. Liss, Inc., pp. 77-96, 1983). Such antibodies can be of any immunoglobulin class, including IgG, IgM, IgE, IgA, IgD, and any subclass thereof. The hybridoma producing the monoclonal antibodies of the invention can be cultivated in vitro and in vivo.

Antibody fragments that have specific binding affinity for a SULT1A3 allozyme can be generated by known techniques. For example, such fragments include but are not limited to $F(ab')_2$ fragments that can be produced by pepsin digestion of the antibody molecule, and Fab fragments that can be generated by reducing the disulfide bridges of $F(ab')_2$ fragments. Alternatively, Fab expression libraries can be constructed. See, for example, Huse et al., *Science*, 246:1275 (1989). Once produced, antibodies or fragments thereof are tested for recognition of SULT1A3 allozymes by standard immunoassay methods including ELISA techniques, radioimmunoassays and Western blotting. See, *Short Protocols in Molecular Biology*, Chapter 11, Green Publishing Associates and John Wiley & Sons, edited by Ausubel et al., 1992.

Methods of the Invention

As a result of the present invention, it is possible to determine sulfonator status of a mammal (e.g., a human subject) as well as to determine if particular SNPs are linked to a particular disease or clinical condition. In some embodiments, it is possible to determine whether a mammal is predisposed (i.e., has a relative greater risk) to, for example schizophrenia, affective disorders, or renal disease. "Sulfonator status" refers to the ability of a mammal to transfer a sulfate group to a substrate (e.g., dopamine). "Predisposition" refers to a relative greater risk for a condition such as schizophrenia. Additional risk factors including, for example, family history of schizophrenia and other genetic factors can be considered when determining risk. Predisposition to a condition such as schizophrenia can be determined based on the presence or absence of a single sulfotransferase sequence variant or based on a variant profile. "Variant profile" refers to the presence or absence of a plurality (e.g., two or more) of SULT1A3 nucleotide sequence variants or SULT1A3 amino acid sequence variants. For example, a variant profile can include the complete SULT1A3 haplotype of the mammal or can include the presence or absence of a set of common non-synonymous SNPs (e.g., single nucleotide substitutions that alter the amino acid sequence of a SULT1A3 polypeptide). In one embodiment, a variant profile includes the presence or absence of two or more non-synonymous SNPs (e.g., two, three, four, or more than four non-synonymous SNPs) described herein. For example, a variant profile can include the presence of variants at nucleotides 99 and 105 relative to the guanine in the splice donor site of intron 1C, or at nucleotide 99 relative to the guanine in the splice donor site of intron 1C and nucleotide 843 relative to the adenine in the SULT1A3 translation initiation site. There may be ethnic-specific pharmacogenetic variation, as certain of the nucleotide and amino acid sequence variants described herein were detected solely in African-American subjects, while other variants were detected only in Caucasian subjects. In addition, the variant profile can include the presence or absence of any type of SULT1A3 SNP together with any other SULT1A3 SNP (e.g., a polymorphism pair or a group of polymorphism pairs). Such polymorphism pairs include, without limitation, those pairs described in Table 4.

Methods to determine whether a mammal is predisposed to a condition such as schizophrenia, an affective disorder, or renal disease can include providing a biological sample from a mammal and detecting the presence or absence of a SULT1A3 nucleotide sequence variant in the sample. In another embodiment, a method can involve providing a biological sample from a mammal and detecting the presence or absence of a plurality of SULT1A3 nucleotide sequence variants in the sample to obtain a variant profile of the mammal. Such methods also can include communicating the variant profile or the presence or absence of a SULT1A3 nucleotide sequence variant to a medical or research professional, to assist that professional in determining whether the mammal is predisposed to a condition such as schizophrenia, an affective disorder, or renal disease.

Articles of Manufacture

The invention also provides articles of manufacture that include populations of isolated SULT1A3 nucleic acid molecules or SULT1A3 polypeptides immobilized on a substrate. Suitable substrates can provide a base for the immobilization of the nucleic acids or polypeptides, and in some embodiments, allow immobilization of nucleic acids or polypeptides into discrete regions. In embodiments in which the substrate includes a plurality of discrete regions, different populations of isolated nucleic acids or polypeptides can be immobilized in each discrete region. Thus, each discrete region of the substrate can include a different SULT1A3 nucleotide or SULT1A3 amino acid sequence variant. Such articles of manufacture can include two or more nucleotide or amino acid sequence variants, or can include all of the sequence variants known for SULT1A3. Furthermore, nucleic acid molecules containing sequence variants for other sulfotransferases, such as SULT1A1, SULT1A2, SULT1B1, and SULT2B1, can be included on the substrate. See, WO 99/64630 and WO 00/20605 for a description of other SULT sequence variants.

Suitable substrates can be of any shape or form and can be constructed from, for example, glass, silicon, metal, plastic, cellulose, or a composite. For example, a suitable substrate can include a multiwell plate or membrane, a glass slide, a chip, or polystyrene or magnetic beads. Nucleic acid molecules or polypeptides can be synthesized in situ, immobilized directly on the substrate, or immobilized via a linker, including by covalent, ionic, or physical linkage. Linkers for immobilizing nucleic acids and polypeptides, including reversible or cleavable linkers, are known in the art. See, for example, U.S. Pat. No. 5,451,683 and WO98/20019. Immobilized nucleic acid molecules typically are about 20 nucleotides in length, but can vary from about 10 nucleotides to about 1000 nucleotides in length.

In practice, a sample of DNA or RNA from a subject can be amplified, the amplification product hybridized to an article of manufacture containing populations of isolated nucleic acid molecules in discrete regions, and any hybridization can be detected. Typically, the amplified product is labeled to facilitate detection of hybridization. See, for example, Hacia et al. (1996) *Nature Genet.* 14:441-447; and U.S. Pat. Nos. 5,770,722 and 5,733,729.

The invention will be further described in the following examples, which do not limit the scope of the invention described in the claims.

EXAMPLES

Example 1

Methods and Materials: PCR Amplification and DNA Sequencing

Genomic DNA from 60 African American blood donors and 60 Caucasian blood donors was obtained from Coriell Cell Repositories (Camden, N.J.). The DNA was used as a PCR template with SULT1A3-specific primers. The three non-coding and seven coding exons in the SULT1A3 gene were amplified from each of the 120 DNA samples using primers that flanked the exons and that would produce amplification products 400-500 by in length. Amplification of the entire gene required seven separate reactions for each DNA sample. The hybridization location of each primer was chosen to avoid repetitive sequence and to ensure amplification specificity. All forward primers contained the M13 forward sequence, and all reverse primers contained the M13 reverse sequence for use in dye primer DNA sequencing. The sequences and locations of each primer within the gene are listed in Table 1 ("F" represents forward; "R", reverse; "U", upstream; "D", downstream; "I", intron; "FR", flanking region; and "UTR", untranslated region).

Following amplification, the products from each reaction were sequenced using dye primer DNA sequencing chemistry to identify heterozygous bases. DNA sequencing was performed in the Mayo Clinic Molecular Biology Core Facility with an Applied Biosystems Model 377 DNA sequencers and BigDye™ (Perkin Elmer, Foster City, Calif.) dye primer sequencing chemistry. In all cases, both DNA strands were sequenced.

DNA sequence analysis: The seven separate SULT1A3 PCR amplifications performed for each of the 120 individual human genomic DNA samples described above generated a total of approximately 900,000 by of sequence. The DNA chromatograms for this sequence were analyzed both visually and using PolyPhred 3.0, Consed 8.0, and GCG 10.0 software. All sequences were compared to the SULT1A3 gene sequences of GenBank accession number U20499.

COS-1 cell expression: Two different SULT1A3 expression constructs were made using the pCR3.1 expression vector. One of the constructs was designed to express the SULT1A3 Lys234Asn allozyme, while the remaining construct was designed to express a wild type SULT1A3 polypeptide. All SULT1A3 cDNA sequences containing SULT1A3 nucleotide sequence variants used to create the expression constructs were created by site directed mutagenesis using the method described by Ho et al. (1989) *Gene* 77:51-59. Each SULT1A3 cDNA was amplified by PCR and subcloned into the eukaryotic expression vector pCR3.1 (Promega, Madison, Wis.). After subcloning, all inserts were sequenced to assure that no spurious nucleotide point mutations had been introduced during the PCR amplifications. COS-1 cells were transfected with these expression constructs by the TransFast™ reagent (Promega, Madison, Wis.) as suggested by the manufacturer (i.e., using a 1:1 charge ratio). As a control, a transfection also was performed with "empty" pCR3.1, i.e., vector lacking an insert, to make it possible to correct for endogenous COS-1 cell SULT activity. The control plasmid pSV-β-galactosidase (Promega) was cotransfected with each SULT1A3 construct to make it possible to correct for transfection efficiency. Two independent transfections, each consisting of three separate plates, were performed with each of the expression constructs. After 48 hours in culture, the transfected cells were harvested and high speed supernatant (HSS) cytosol preparations were prepared as described by Wood et al. (1994) *Biochem. Biophys. Res. Commun.* 198:1119-1127. Aliquots of these cytosol preparations were stored at −80° C. prior to assay.

Enzyme Assays: β-galactosidase activity in each of the COS-1 HSS preparations was measured with the β-galactosidase Enzyme Assay System (Promega, Madison, Wis.). These HSS preparations of recombinant SULT1A3 allozyme were used for the activity studies without any further purification. The protein concentration of each recombinant protein preparation was determined by the dye-binding method of Bradford with bovine serum albumin (BSA) as a standard.

SULT1A3 enzyme activity was measured with an assay that involves sulfate conjugation of a sulfate acceptor substrate, dopamine (40 μM), in the presence of the sulfate donor 3'-phosphoadenosine-5'-phosphosulfate (PAPS). Blank samples did not contain dopamine. Cytosol from COS-1 cells transfected with empty pCR3.1 were used to correct for endogenous SULT activity. Because SULTs display profound substrate inhibition, a range of dopamine concentrations were tested to ensure that the assays were performed at a dopamine concentration that yielded maximal activity for the Lys234Asn allozyme. Enzyme activity was expressed as nanomoles (nmoles) of sulfate conjugated product formed per hour of incubation. Apparent $K_m$ values for PAPS were determined in the presence of dopamine, with PAPS concentrations that varied from 0.035 μM to 0.5 μM and dopamine concentrations that varied from 2.5 μM to 80 μM.

Data Analysis: Apparent $K_m$ values were calculated by using the method of Wilkinson with a computer program written by Cleland. Wilkinson, *Biochem. J.*, 80:324-332 (1961); and Cleland, *Nature*, 198:463-365 (1963). Statistical comparisons of data were performed by ANOVA with the StatView program, version 4.5 (Abacus Concepts, Inc., Berkeley, Calif.). Linkage analysis was performed after all DNA samples had been genotyped at each of the 6 polymorphic sites observed. D' values, a quantitative method for reporting linkage data that is independent of allele frequency (Hartl and Clark, *Principles of Population Genetics*, 3$^{rd}$ ed. (1997) Sinauer Associates, Inc., (Sunderland, Mass.), pp. 96-106; and Hedrick, *Genetics of Populations*, 2$^{nd}$ ed. (2000) Jones and Bartlett (Sudbury, Mass.), pp. 396-405), then were calculated. The genotype data also were used to assign inferred haplotypes using a program based on the E-M algorithm (Long et al. (1995) *Am. J. Hum. Genet.* 56:799-810; and Excoffier and Slatkin (1995) *Mol. Biol. Evol.* 12:921-927). Unambiguous haplotype assignment also was possible on the basis of genotype for samples that contained no more than one heterozygous polymorphism.

Western blot analysis: Quantitative Western blot analysis was performed with recombinant SULT1A3 protein. The quantity of cytosol loaded on the gel for each allozyme was adjusted so that each lane contained an equal quantity of β-galactosidase activity and thus gel loading was corrected for variation in transfection efficiency. Properties of the antibody used to detect the SULT1A3 protein have been described elsewhere. Bound antibody was detected using the ECL system (Amersham Biosciences). The Ambis densitometric system was used to quantitate immunoreactive protein in each lane, and those data were expressed as a percent of the intensity of the control wild type SULT1A3 protein band on that gel.

TABLE 1

PCR primers used for resequencing SULT1A3

| Primer Name | Primer Location | Primer Sequence | SEQ ID NO: |
|---|---|---|---|
| UF(−4118)M13 | 5'-FR | <u>TGTAAAACGACGGCCAGTT</u>AATGGACGATGGGTGCCTTGTACT | 5 |
| UR(−3699)M13 | 5'-FR | <u>CAGGAAACAGCTATGACC</u>ATGGGCCCTTAGCAGG | 6 |
| UF(−3833)M13 | 5'-FR | <u>TGTAAAACGACGGCCAGTT</u>GTAATGCCCGCAACAGTGC | 7 |
| UR(−3532)M13 | 5'-FR | <u>CAGGAAACAGCTATGACC</u>TAGGCGGGGGTAAGGACACTGAGGCTCA | 8 |
| UF(−1705)M13 | 5'-FR | <u>TGTAAAACGACGGCCAGT</u>CAATACCAATGTTGGCCCCTTTTG | 9 |
| UR(−1212)M13 | 5'-FR | <u>CAGGAAACAGCTATGACC</u>CACCCTGTCTCAAAAATACACAAAGG | 10 |
| I1F(−391)M13 | Intron 1 | <u>TGTAAAACGACGGCCAGT</u>AGCAAAAAACTCTGCAAAGGGGC | 11 |
| I2R52M13 | Intron 2 | <u>CAGGAAACAGCTATGACC</u>ACCAAGGTGGGGACTGCCG | 12 |
| I2F135M13 | Exon 2 | <u>TGTAAAACGACGGCCAGT</u>ACACCTACCCCAAGTCT | 13 |
| I4R120M13 | Intron 4 | <u>CAGGAAACAGCTATGACC</u>TGGATGTCATCTCTACAGCA | 14 |
| I4F(−151)M13 | Intron 4 | <u>TGTAAAACGACGGCCAGT</u>CGAGCAGGGTTCAGATCCCAG | 15 |
| I6R116M13 | Intron 6 | <u>CAGGAAACAGCTATGACC</u>GAATCCGGGCTTCGTGTGGGAG | 16 |
| I6F(−34)M13 | Intron 6 | <u>TGTAAAACGACGGCCAGT</u>GTTTTGCTCCACTGAGGAGCCC | 17 |
| DR1048M13 | Exon 8 (3'-UTR) | <u>CAGGAAACAGCTATGACC</u>TGAAATTCGTGGCCTATT | 18 |

Underlined nucleotides indicate M113 tag

Example 2

SULT1A3 Polymorphisms

Sequencing of the 5' and 3' untranslated sequences, exons, and introns of the SULT1A3 nucleic acid revealed nine SNPs (Table 2). Polymorphisms in exons, untranslated regions (UTR), and flanking regions (FR) are numbered relative to the adenine in the SULT1A3 translation initiation codon (ATG, adenine is +1). Polymorphisms in introns are numbered separately, either as positive numbers relative to the guanine in the splice donor site (GT, guanine is +1), or as negative numbers relative to the guanine in the splice acceptor site (AG, guanine is −1). One of the nine SNPs altered the encoded amino acid (i.e., a non-synonymous SNP), resulting in two different SULT1A3 allozymes. This variant appeared to be "common" (frequency≧1%, Table 2) among the 60 African American samples. The same variant was not detected among the 60 Caucasian samples.

The average number of polymorphisms present in the gene overall, within the ORF, and outside the ORF was 2.2, 2.3, and 2.1 per kb sequenced, respectively, in the African American samples, and 1.3, 0.8, and 1.7 per kb sequenced, respectively, in the Caucasian samples (Table 3). For purposes of comparison, Table 3 also includes data from a large study of polymorphism frequencies in 74 human genes (Halushka et al. (1999) *Nat. Genet.* 22:239-247). Because Halushka et al. studied a slightly smaller number of samples (74 versus the 120 described), low frequency polymorphisms that would not have been detected by Halushka et al. have been eliminated because of their lower sample number. The genetic variation present within the SULT1A3 sequence was very similar to average values observed in the 74 genes sequenced by Halushka et al. The data in Table 3 also are presented by gene region, with "UTR" representing both exons encoding cDNA untranslated regions and 5'- and 3'-flanking regions.

TABLE 2

Human SULT1A3 sequence variants

| Polymorphism Position | Location In Gene | WT Sequence Nucleotide | Variant Sequence Nucleotide | AA | CA |
|---|---|---|---|---|---|
| I1C(96) | 5'-FR | C | T | 0.000 | 0.008 |
| I1C(99) | 5'-FR | G | C | 0.660 | 0.500 |
| I1C(105) | 5'-FR | C | T | 0.017 | 0.050 |
| I1A(1325) | 5'-FR | A | G | 0.075 | 0.000 |
| 105 | Exon 2 | A | G | 0.033 | 0.108 |
| 14(1369) | Intron 4 | G | A | 0.008 | 0.000 |
| 702 | Exon 7 | G | T | 0.042 | 0.000 |
| I7 (113) | Intron 7 | C | T | 0.008 | 0.042 |
| 843 | Exon 8 | G | A | 0.083 | 0.000 |

TABLE 3

SULT1A3 polymorphism frequencies

| | Polymorphisms per kb | | |
|---|---|---|---|
| | SULT1A3 | | |
| | African American | Caucasian | 74 Human Genes |
| Gene(s) | 1 | 1 | 74 |
| Samples | 60 | 60 | 75 |
| Min. Allele Freq. | 0.8 | 0.8 | 0.68% |
| Overall | 2.2 | 1.3 | 4.6 |
| Coding | 2.3 | 0.8 | 4.4 |
| Noncoding | 2.1 | 1.7 | 5.9 |
| UTRs | 1.5 | 1.5 | 4.4 |
| Introns | 2.6 | 1.3 | 6.0 |

Example 3

Linkage Disequilibrium and Haplotype Analysis

Linkage disequilibrium analysis was performed after all of the DNA samples had been genotyped at each of the nine polymorphic sites. Pairwise combinations of these polymorphisms were tested for linkage disequilibrium using the EH program developed by Terwilliger and Ott, *Handbook of Human Genetic Linkage*, The Johns Hopkins University Press, Baltimore, pp. 188-193 (1994). The output of this program was used to calculate d' values, a method for reporting linkage data that is independent of sample size. All pairwise combinations with a linkage disequilibrium greater than or equal to 0.75% are shown in Table 4.

Two unequivocal haplotypes were identified by these studies. As shown in Table 5, the haplotype analysis accounted for 8.4% and 5% of all samples based on these unequivocal haplotypes for DNA samples from African-American and Caucasian-American subjects, respectively. The unequivocal haplotypes included one that was common to both ethnic groups and another that was ethnic-specific for African-American subjects.

TABLE 4

SULT1A3 linkage disequilibrium analysis

| Polymorphism Pair African American | | d' Value | $\chi^2$ Value |
|---|---|---|---|
| I1C99 | I1A(1325) | −1 | 0.031074 |
| I1C99 | 843 | 0.776 | 0.017388 |
| 702 | I7113 | 1 | 0.022897 |

| Polymorphism Pair Caucasian American | | d' Value | P Value |
|---|---|---|---|
| I1C99 | 105 | −1 | 0.002786 |

TABLE 5

SULT1A3 haplotype analysis

| African American Frequency | Caucasian American Frequency | I1C99 | I1C105 | 843 |
|---|---|---|---|---|
| 0.067 | 0.000 | V | WT | V |
| 0.017 | 0.050 | V | V | WT |

Example 4

Activity and Immunoreactivity of Lys234Asn Allozyme

Cell homogenate preparations containing recombinant SULT1A3 Lys234Asn allozyme, prepared as described in Example 1, were used to assess catalytic activity. The resulting activities were adjusted to a percentage of the WT SULT1A3 enzyme activity. Lys234Asn exhibited a 73% reduction in enzyme activity, displaying only 27% of WT activity. These cell preparations contained similar levels of β-galactosidase activity, indicating that the enzyme activity results were not the result of low transfection efficiency.

To determine whether the decreased activity of the Lys234Asn SULT1A3 variant might be related to quantity of immunoreactive enzyme protein, quantitative Western blot analyses were conducted. The decrease in enzyme activity for the Lys234Asn allozyme was paralleled by a similar reduction in the level of immunoreactive protein.

Example 5

Substrate Kinetic Studies

Alterations in amino acid sequence can alter enzyme substrate affinity and/or catalytic efficiency. Substrate kinetic studies were conducted to determine whether the Lys234Asn allozyme differed from the WT SULT1A3 protein in these aspects. A series of dopamine and PAPS concentrations were used to estimate apparent $K_m$ values for recombinant wild type SULT1A3 and for the Lys234Asn variant allozyme. These studies revealed no significant difference in apparent $K_m$ values for either dopamine (10.4 μM vs. 9.8 μM for WT and Lys234Asn, respectively) or PAPS (0.112 μM vs. 0.107 μM for WT and Lys234Asn, respectively). These results raise the possibility of ethnic-specific genetic alterations of catecholamine sulfation in humans.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated human sulfotransferase 1A3 (SULT1A3) polypeptide comprising the amino acid sequence set forth in SEQ ID NO: 4, wherein the amino acid at position 234 is a variant residue.

2. The isolated SULT1A3 polypeptide of claim 1, wherein said variant residue is asparagine.

* * * * *

UNITED STATES PATENT AND TRADEMARK OFFICE
CERTIFICATE OF CORRECTION

| | | |
|---|---|---|
| PATENT NO. | : 7,745,185 B1 | Page 1 of 1 |
| APPLICATION NO. | : 12/127110 | |
| DATED | : June 29, 2010 | |
| INVENTOR(S) | : Bianca A. Thomae et al. | |

It is certified that error appears in the above-identified patent and that said Letters Patent is hereby corrected as shown below:

Title Page item (73) Assignee, please delete "NM" and insert --MN-- therefor.

Signed and Sealed this
Fourth Day of January, 2011

David J. Kappos
*Director of the United States Patent and Trademark Office*